US012605336B2

(12) United States Patent
Sailor et al.

(10) Patent No.: US 12,605,336 B2
(45) Date of Patent: Apr. 21, 2026

(54) FUSOGENIC LIPOSOME-COATED POROUS SILICON NANOPARTICLES

(71) Applicant: The Regents of the University of California, Oakland, CA (US)

(72) Inventors: Michael J. Sailor, La Jolla, CA (US); Byungji Kim, Cambridge, MA (US); Jinyoung Kang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 554 days.

(21) Appl. No.: 17/871,768

(22) Filed: Jul. 22, 2022

(65) Prior Publication Data

US 2023/0095861 A1 Mar. 30, 2023

Related U.S. Application Data

(63) Continuation of application No. 16/920,979, filed on Jul. 6, 2020, now Pat. No. 11,406,597, which is a (Continued)

(51) Int. Cl.
*A61K 9/1272* (2025.01)
*A61K 9/00* (2006.01)
(Continued)

(52) U.S. Cl.
CPC .......... *A61K 9/1272* (2013.01); *A61K 9/0048* (2013.01); *A61K 9/0051* (2013.01); (Continued)

(58) Field of Classification Search
CPC .................................................... A61K 9/1272
See application file for complete search history.

(56) References Cited

U.S. PATENT DOCUMENTS

| | | | |
|---|---|---|---|
| 2,674,743 | A | 4/1954 | Gaiser et al. |
| 3,828,777 | A | 8/1974 | Ness |

(Continued)

FOREIGN PATENT DOCUMENTS

| | | |
|---|---|---|
| AU | 753542 | 2/2000 |
| CA | 2228426 | 2/1997 |

(Continued)

OTHER PUBLICATIONS

Nilton Lincopan et al. "Silica-based cationic bilayers as immunoadjuvants." BMC Biotechnology, vol. 9:5, 2009, pp. 1-19. (Year: 2009).*

(Continued)

*Primary Examiner* — Isaac Shomer
(74) *Attorney, Agent, or Firm* — Gavrilovich, Dodd & Lindsey LLP

(57) ABSTRACT

The disclosure describes a fusogenic liposome-coated porous silicon nanoparticles for high loading efficiency of anionic payloads (small molecules, dyes, nucleic acids), and for non-endocytic delivery of hydrophilic and lipophilic payloads by membrane fusion. The liposome coating can be further modified with targeting peptides or antibodies via covalent binding chemistry between the ligands and functionalized poly(ethylene glycol). The surface moieties can be transferred to the cellular membrane surface by fusogenic uptake. The composition of the disclosure can be applied in the treatment of diseases by delivering entrapped/encapsulated payloads.

18 Claims, 11 Drawing Sheets

Specification includes a Sequence Listing.

Related U.S. Application Data continuation of application No. 15/741,649, filed as application No. PCT/US2016/041639 on Jul. 8, 2016, now Pat. No. 10,702,474.

(60) Provisional application No. 62/190,705, filed on Jul. 9, 2015.

(51) Int. Cl.

| | |
|---|---|
| ***A61K 9/1271*** | (2025.01) |
| ***A61K 9/51*** | (2006.01) |
| ***A61K 31/713*** | (2006.01) |
| ***A61K 47/64*** | (2017.01) |
| ***A61K 47/69*** | (2017.01) |
| ***B82Y 5/00*** | (2011.01) |
| ***B82Y 30/00*** | (2011.01) |

(52) U.S. Cl.

CPC .......... *A61K 9/5115* (2013.01); *A61K 31/713* (2013.01); *A61K 47/64* (2017.08); *A61K 47/6923* (2017.08); *A61K 9/1271* (2013.01); *B82Y 5/00* (2013.01); *B82Y 30/00* (2013.01)

(56) References Cited

U.S. PATENT DOCUMENTS

| | | | | |
|---|---|---|---|---|
| 5,242,950 | A | 9/1993 | Hastings | |
| 6,322,895 | B1 | 11/2001 | Winget et al. | |
| 6,666,214 | B2 | 12/2003 | Canham | |
| 6,770,480 | B1 | 8/2004 | Canham | |
| 6,929,950 | B2 | 8/2005 | Canham et al. | |
| 7,332,339 | B2 | 2/2008 | Canham et al. | |
| 7,638,137 | B2 | 12/2009 | Chauhan et al. | |
| 7,763,277 | B1 | 7/2010 | Canham et al. | |
| 8,088,401 | B2 | 1/2012 | Saffie et al. | |
| 8,097,236 | B2 | 1/2012 | Aston et al. | |
| 8,147,864 | B2 | 4/2012 | Canham et al. | |
| 8,293,630 | B2 | 10/2012 | Dunkley et al. | |
| 8,303,975 | B2 | 11/2012 | Canham et al. | |
| 8,313,761 | B2 | 11/2012 | Canham et al. | |
| 8,318,194 | B2 | 11/2012 | Canham et al. | |
| 8,361,491 | B2 | 1/2013 | Canham et al. | |
| 8,992,984 | B1 | 3/2015 | Brinker | |
| 10,702,474 | B2 * | 7/2020 | Sailor .................. | A61K 9/0051 |
| 11,406,597 | B2 * | 8/2022 | Sailor .................. | A61K 9/5115 |
| 2002/0156274 | A1 | 10/2002 | Terfloth | |
| 2003/0060878 | A1 | 3/2003 | Shadduck et al. | |
| 2003/0146109 | A1 | 8/2003 | Sailor et al. | |
| 2004/0052867 | A1 | 3/2004 | Canhann | |
| 2004/0244889 | A1 | 12/2004 | Sailor et al. | |
| 2005/0009374 | A1 | 1/2005 | Gao et al. | |
| 2005/0025820 | A1 | 2/2005 | Kester et al. | |
| 2005/0042764 | A1 | 2/2005 | Sailor et al. | |
| 2005/0101026 | A1 | 5/2005 | Sailor et al. | |
| 2005/0181049 | A1 | 8/2005 | Dong et al. | |
| 2006/0236436 | A1 | 10/2006 | Li et al. | |
| 2006/0255008 | A1 | 11/2006 | Link et al. | |
| 2007/0154522 | A1 | 7/2007 | Chow et al. | |
| 2009/0208556 | A1 | 8/2009 | Freeman et al. | |
| 2011/0203013 | A1 | 8/2011 | Peterson et al. | |
| 2012/0171292 | A1 * | 7/2012 | Sailor ................ | A61K 47/6929 977/773 |
| 2013/0064965 | A1 | 3/2013 | Canham et al. | |
| 2014/0079774 | A1 | 3/2014 | Brinker et al. | |
| 2015/0037427 | A1 | 2/2015 | Benita et al. | |

FOREIGN PATENT DOCUMENTS

| | | | | |
|---|---|---|---|---|
| CA | 2368679 | | 11/2000 | |
| CA | 2228426 | C | 2/2008 | |
| CA | 2328996 | C | 12/2012 | |
| CN | 99809028.X | | 8/2001 | |
| CN | 00809693.7 | | 8/2002 | |
| CN | 103687590 | A | 3/2014 | |
| EP | 842113 | A | 5/1998 | |
| EP | 1407764 | A1 | 4/2004 | |
| EP | 1071398 | B1 | 5/2004 | |
| EP | 1776949 | A2 | 4/2007 | |
| EP | 2269574 | A2 | 1/2011 | |
| GB | 9909996.2 | | 5/1999 | |
| NZ | 509142 | | 1/2004 | |
| NZ | 515189 | | 5/2004 | |
| WO | 1997006101 | | 2/1997 | |
| WO | 98/16202 | A2 | 4/1998 | |
| WO | 00/05339 | A1 | 2/2000 | |
| WO | 2000066190 | | 11/2000 | |
| WO | 200215863 | A1 | 2/2002 | |
| WO | 2003067231 | A1 | 8/2003 | |
| WO | 2004071949 | | 8/2004 | |
| WO | 2005034725 | | 4/2005 | |
| WO | 2006044957 | A2 | 4/2006 | |
| WO | 2006/050221 | A2 | 5/2006 | |
| WO | 2009/009563 | A9 | 1/2009 | |
| WO | WO-2013056132 | A2 * | 4/2013 | ............. A61P 31/12 |

OTHER PUBLICATIONS

Carlee E. Ashley et al. "Delivery of Small Interfering RNA by Peptide-Targeted Mesoporous Silica Nanoparticle-Supported Lipid Bilayers." ACS Nano, vol. 6, No. 3, 2012, pp. 2174-2188 and 5 pages of supplemental information. (Year: 2012).*

Emily J. Anglin, Lingyun Cheng, William R. Freeman, and Michael J. Sailor. "Porous silicon in drug delivery devices and materials." Advanced Drug Delivery Reviews, vol. 60, 2008, pp. 1266-1277. (Year: 2008).*

AJ Salinas, M Vallet-Regi, and I Izquierdo-Barba. "Biomimetic Apatite Deposition on Calcium Silicate Gel Glasses." Journal of Sol-Gel Science and Technology 21, 2001, pp. 13-25. (Year: 2001).*

Priya Saravanapavan and Larry L. Hench. "Mesoporous calcium silicate glasses. I. Synthesis." Journal of Non-Crystalline Solids 318 (2003), pp. 1-13. (Year: 2003).*

Tadashi Kokubo, Hyun-Min Kim, and Masakazu Kawashita. "Novel bioactive materials with different mechanical properties." Biomaterials, vol. 24 (2003), pp. 2161-2175. (Year: 2003).*

Anglin et al., "Engineering the chemistry and nanostructure of porous silicon fabry-perot films for loading and release of a steroid," Langmuir, Oct. 2004, pp. 11264-11269, vol. 20, No. 25.

Charney et al., "Inclusion of ibuprofen in mesoporous templated silica: drug loading and release property," European J. of Pharm. and Biopharm., May 2004, pp. 533-540, vol. 57, No. 3.

Cohen et al., "Microfabrication of Silicon-Based Nanoporous Particulates for Medical Applications," Biomedical Microdevices, 5:3, pp. 253-259, published 2003.

Lai et al., "A Mesoporous Silica Nanosphere-Based Carrier System with Chemically Removable CdS Nanoparticle Caps for Stimuli-Responsive Controlled Release of Neurotransmitters and Drug Molecules," Journal of American Chemical Society, 125, pp. 4451-4459, published on web Mar. 20, 2003.

Li, Yang Yang, et al., "Polymer replicas of photonic porous silicon for sensing and drug delivery applications," Science, 2003, vol. 299, pp. 2045-2047.

Madou, Marc J. "Fundamentals of Microfabrication: The Science of Miniaturization", Second Edition, 2002, pp. 228-232.

Mortemousque et al., S/e-PTFE Episcleral Buckling Implants: An Experimental and Histophathologic Study, Journal of Biomedical Materials Research, 63, pp. 686-691, Published 2002.

Qin et al., "Size Control of Porous Silicon Nanoparticles by Electrochemical Perforation Etching," Part. Part. Syst. Charact., 31:252-256, 2014.

Rysiakiewicz-Pasek et al.,, "Effect of potassium nitrate treatment on the adsorption properties of silica porous glasses," J. of Non-Crystalline Solids, Oct. 2004, pp. 260-264, vol. 345-346.

Sailor, Michael et al. "Biomolecular screening with encoded porous-silicon photonic crystals", Nature Materials, vol. 1, published online Sep. 2, 2002, pp. 39-41.

Schifferer, Hermann, Extended European Search Report, European Patent Office, Application No. 16822074.7, Mar. 27, 2019.

(56) References Cited

OTHER PUBLICATIONS

Voskoglou-Nomikos et al., Clinical Cancer Resarch, vol. 9, pp. 4227-4239, 2003.
Wittmann-Regis, Agnes, International Preliminary Report on Patentability and Written Opinion, PCT/US2016/041639, Jan. 18, 2018.
Young, Lee W., International Search Report and Written Opinion, PCT/US2016/041639, Sep. 16, 2016.
Zhang, Zheng, Office Action, China National Intellectual Property Administration, Application No. 201680047665.5, Jun. 19, 2020.

* cited by examiner

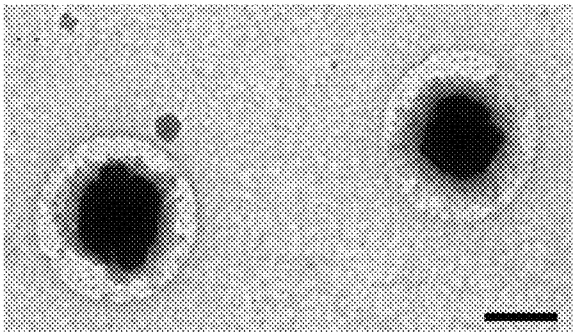
FIG. 1F
| | Average Size (nm) | Zeta-Potential (mV) |
|---|---|---|
| Core pSiNPs | 68.1 ± 5.8 | -21.3 ± 1.0 |
| Fusogenic Ca-pSi (F-Ca-pSi-siRNA) | 187.4 ± 5.2 | 9.8 ± 0.4 |
| Non-fusogenic Ca-pSi (NF-Ca-pSi-siRNA) | 190.8 ± 4.7 | 10.4 ± 1.8 |
FIG. 1G
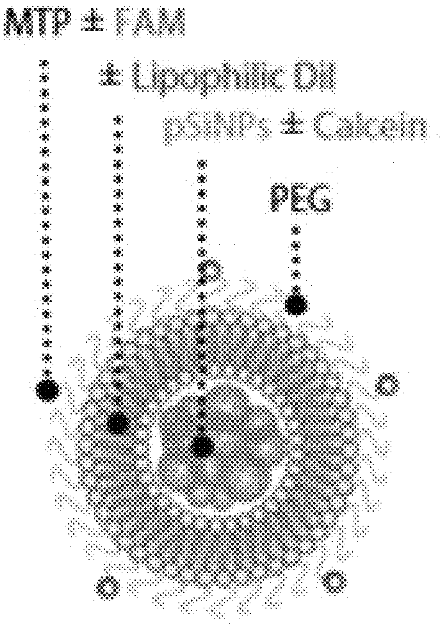
FIG. 1H

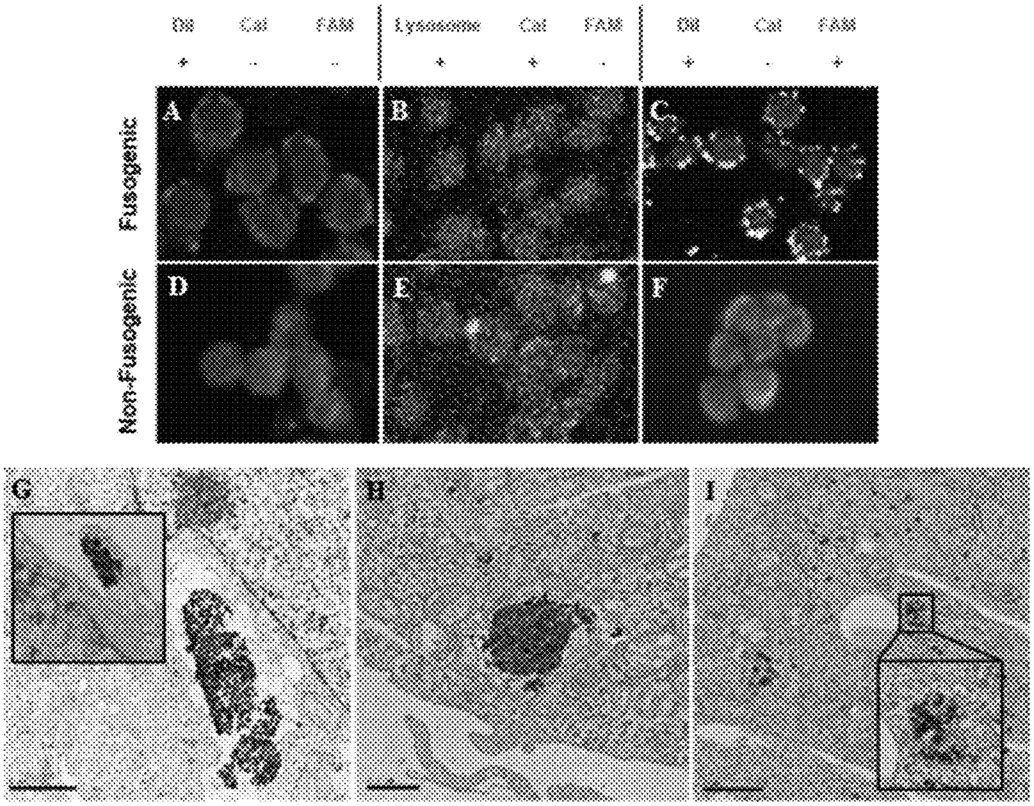
FIG. 4A-I
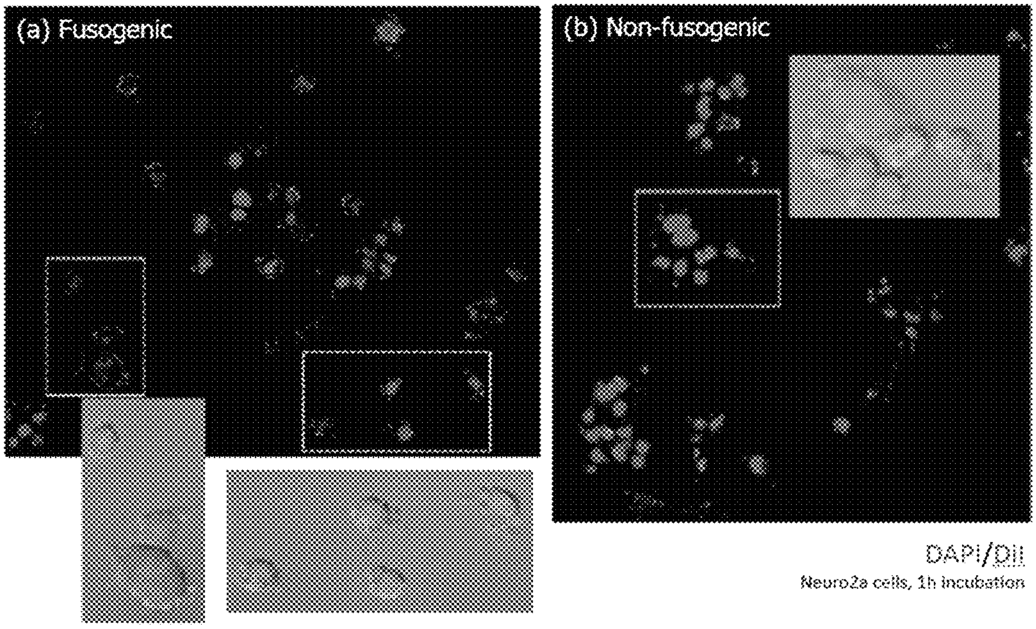
FIGURE 5A-B

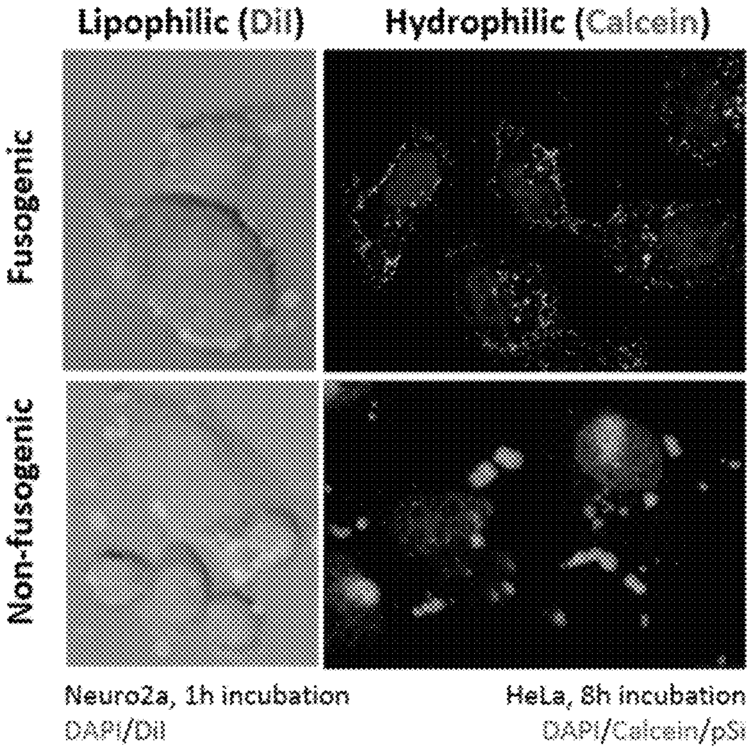
FIGURE 12
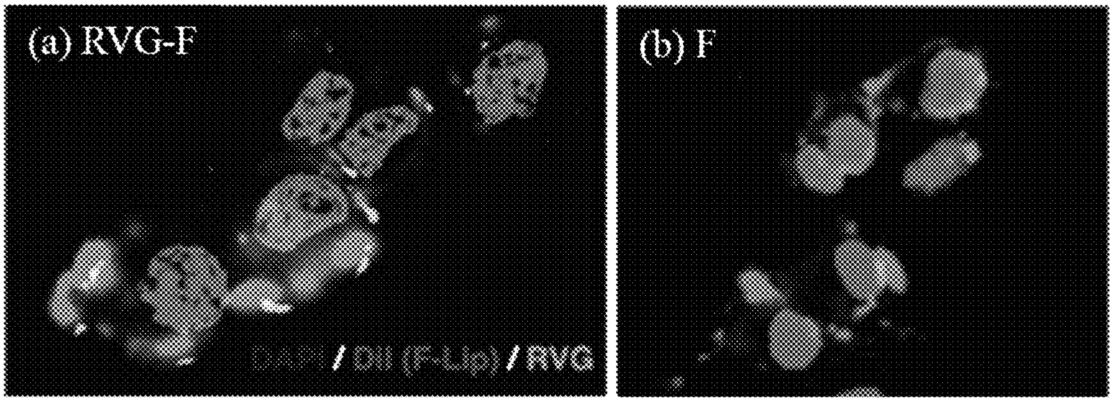
FIGURE 13A-B

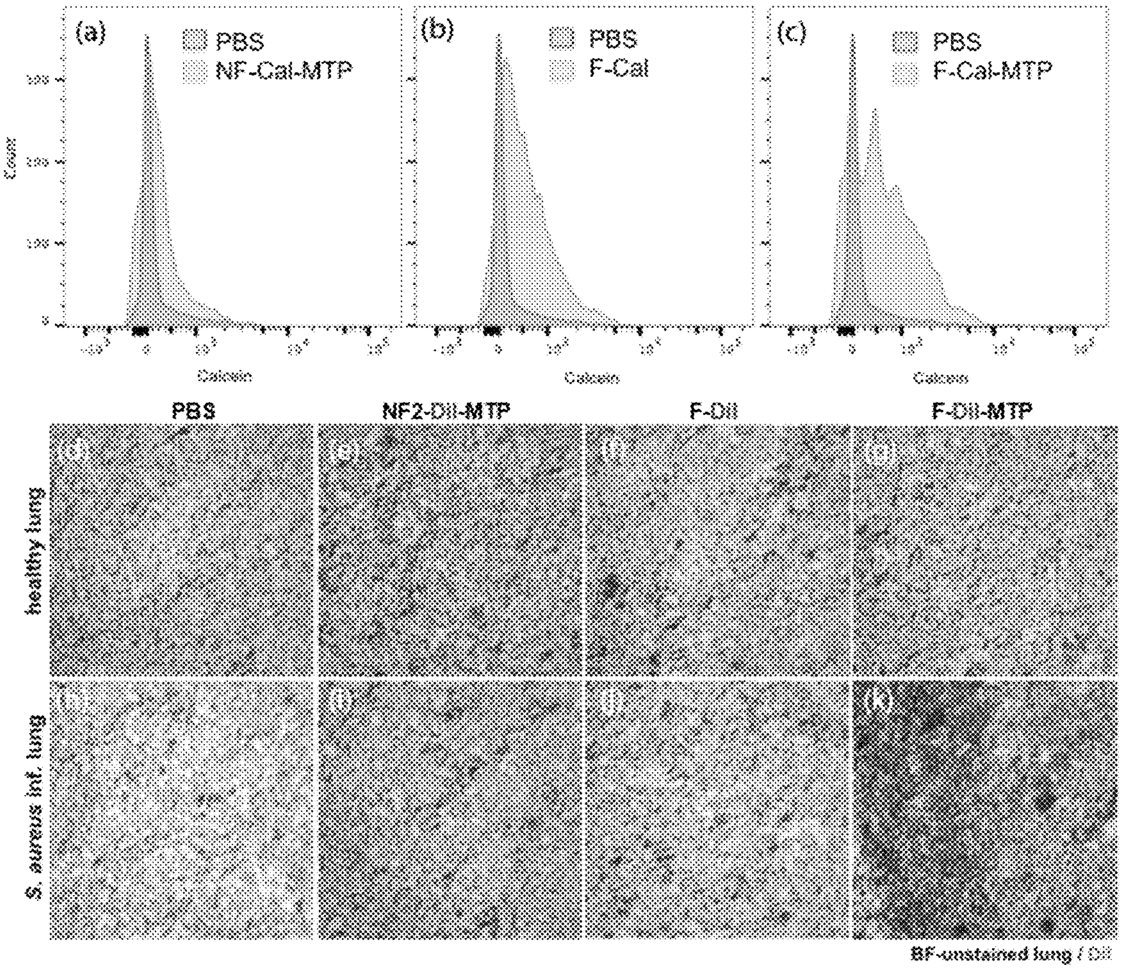
FIGURE 15A-K

FUSOGENIC LIPOSOME-COATED POROUS SILICON NANOPARTICLES

CROSS REFERENCE TO RELATED APPLICATIONS

This application is a continuation of U.S. patent application Ser. No. 16/920,979, filed Jul. 6, 2020 (now U.S. Pat. No. 11,406,597), which application is a continuation of U.S. patent application Ser. No. 15/741,649, filed Jan. 3, 2018 (now U.S. Pat. No. 10,702,474), which is a U.S. National Stage Application filed under 35 U.S.C. § 371 and claims priority to International Application No. PCT/US2016/041639, filed Jul. 8, 2016, which application claims priority under 35 U.S.C. § 119 from Provisional Application Ser. No. 62/190,705, filed Jul. 9, 2015, the disclosures of which are incorporated herein by reference.

STATEMENT AS TO FEDERALLY SPONSORED RESEARCH

This invention was made with government support under Grant No. HR0011-13-2-0017 awarded by the Defense Advanced Research Projects Agency and Grant No. DMR-1210417 awarded by the National Science Foundation. The government has certain rights in the invention.

TECHNICAL FIELD

The invention relates to delivery systems and, more particularly, fusogenic liposomal nanoparticle compositions for delivery of drugs, nucleic acids and peptides to a target cell or tissue.

INCORPORATION BY REFERENCE OF SEQUENCE LISTING

Accompanying this application is a Sequence Listing entitled, "00015-293US3.xml" created on Dec. 16, 2022 and having 1,981 bytes of data, machine formatted on IBM-PC, MS-Windows operating system. The sequence listing is hereby incorporated by reference in its entirety for all purposes.

BACKGROUND

In vivo gene delivery remains a challenge due to low efficiency or cytotoxicity. Cellular endocytosis is the primary uptake pathway of most nanoplatforms, which results in lysosomal degradation of genetic material and low therapeutic efficacy.

SUMMARY

The disclosure provides a biodegradable liposomal porous silicon nanoparticle system that can bypass endocytic uptake via liposome-plasma membrane fusion. Unlike most currently studied nanoparticular delivery systems that allow for endocytic uptake of all its payloads, membrane fusion allows direct release of hydrophilic payloads from the core of liposomes into the cell cytoplasm, transfer of hydrophobic molecules from the liposomal bilayer to the cell membrane bilayer, and transfer of moieties conjugated on the outer surface of liposomes (antibodies, small molecules, peptides, etc.) to the cell membrane surface.

Disclosed are liposomal porous silicon particles and their method of synthesis and applications. The liposome may be loaded with lipophilic payloads, and be functionalized with poly(ethylene glycol) (PEG) and other surface moieties (targeting peptides, antibodies, aptamers, etc.) to transfer them into and on cellular membranes through fusion. A porous silicon-based core can entrap high amounts of payloads (small molecule, protein, nucleic acid), and deliver them directly to the target cell's cytoplasm; by-passing cellular endocytosis can increase delivery and therapeutic efficacy of treatment. In vitro knockdown efficiency comparable to that of Lipofectamine has been demonstrated.

The disclosure provides a fusogenic liposome-coated porous silicon nanoparticle comprising, a nanostructured silicon-containing core material having a plurality of pores, the material comprising, (a) a silicon-containing core, (b) a porous surface that is chemically linked to the core, (c) a plurality of cargo molecules that are physically associated with silicon-containing core material, and (d) a metal silicate; and a fusogenic liposome coating around the silicon-containing core material. In one embodiment, the fusogenic liposome comprises 1,2-dimyristoyl-sn-glycero-3-phosphocholine (DMPC), 1,2-distearoyl-sn-glycero-3-phosphoethanolamine-N-[methoxy(polyethylene glycol)-2000](DSPE-PEG), and 1,2-dioleoyl-3-trimethylammonium-propane (DOTAP). In another embodiment, the silicon-containing core is substantially or completely oxidized silicon. In yet another embodiment of any of the foregoing embodiments, the metal silicate comprises a calcium or magnesium silicate. In a further embodiment, the metal silicate forms a shell on the silicon-containing core. In yet another embodiment, there is no gaps between silicon-containing core and the calcium or magnesium silicate shell. In another embodiment, the plurality of pores are chemically or physically configured to admit a cargo molecule. In yet another embodiment, chemical oxidation of the pore surface in conjunction with the formation of a calcium or magnesium silicate shell results in physical trapping of the plurality of cargo molecules. In still another embodiment, the plurality of pores contain a drug. In another embodiment, the plurality of pores contain a non-drug substance. In another embodiment, the silicon-containing core comprises a molecule that is physically, adsorbed, or covalently trapped by with the plurality of pores, or attached to the plurality of pores, and wherein the silicon-containing core is coated by a calcium or magnesium containing shell formed by the action of aqueous solution of calcium or magnesium ions added to said host material in the presence of the molecule. In yet another embodiment, the fusogenic liposome comprises a mixture of DMPC, DOTAP, and DSPE-PEG (methoxy). In another embodiment, the fusogenic liposome comprises a mixture of DMPC, DOTAP, and DSPE-PEG (carboxy). In another embodiment, the fusogenic liposome comprises a mixture of DMPC, DOTAP, and DSPE-PEG (maleimide). In yet another embodiment, the silicon-containing core material has a hydrodynamic diameter ranging from about 10-100 nm. In another embodiment, the fusogenic liposome has a hydrodynamic diameter ranging from about 100-400 nm. In still yet another embodiment, a targeting molecule is conjugated to the fusogenic liposomal coating. In one embodiment, an antibody is conjugated to the fusogenic liposomal coating. In another embodiment, a hydrophobic cargo molecule is loaded in the fusogenic liposomal coating. In yet another embodiment, a hydrophilic cargo molecule is entrapped within the plurality of pores of the silicon-containing core. In still another embodiment, a hydrophobic agent/cargo molecule is present in the fusogenic coating and a hydrophilic agent/cargo is present in the plurality of pores of the silicon-containing core. In another embodiment, a nucleic acid cargo molecule is entrapped within the plurality of pores of the silicon-containing core. In another embodiment, a small molecule cargo molecule is entrapped within the plurality of pores of the porous silicon-containing core.

The disclosure also provides a method of delivering nucleic acid payloads to cells comprising contacting the cell with a fusogenic liposome-coated porous silicon nanoparticle of the disclosure that contains a nucleic acid.

The disclosure also provides a method of treating a disease or disorder of the eye comprising delivering into or upon a surface of the eye the fusogenic liposome-coated porous silicon nanoparticle of the disclosure.

The disclosure also provides a method for treating cancer comprising delivering into the body the fusogenic liposome-coated porous silicon nanoparticle of the disclosure.

The disclosure also provides a method for treating bacterial infection comprising delivering into the body the fusogenic liposome-coated porous silicon nanoparticle of the disclosure.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A-H show schematics representing embodiments of the disclosure. (A) shows a schematic of action of a fusogenic liposome-coated porous silicon nanoparticle of the disclosure. (B) shows loading of calcium coated porous silicon (pSi) with anionic payloads. Anionic payload and cationic metal-silicate-deposited pSiNPs form a cluster by electrostatic interactions. (C) shows loading of "loaded"-pSi into cationic liposomes. The payload-pSi cluster are encapsulated into cationic fusogenic liposomes via electrostatic interactions and mechanical extrusion. (D) depicts modification of the liposome with targeting peptides. Targeting peptide or antibody can be conjugated to functional PEG via chemical binding. (E) shows low magnification of particles. Imaged using Tecnai TEM. Negative staining done by uranyl acetate. Scale bar indicates 500 nm. (F) shows high magnification of particles show cloudy liposomal coating around dark and dense porous silicon-based core. Imaged using JEOL 1200 EX TEM. Negative staining by 2% PTA. Scale bar indicates 200 nm. (G) a table of particle size and zeta-potential measured by DLS (n=3). (H) shows a schematic of a particle of the disclosure.

FIG. 4A-I shows confocal microscopy and transmission electron microscopy. (A-F) Confocal microscopy of J771A.1; (A) J771A.1 after 10 min incubation with F-pSi loaded with DiI; (B) J774a.1 after 1 h incubation with Lysotracker Red and 10 min incubation with F-pSi with calcein; (C) J774a.1 after 5 min incubation with MTP-FAM conjugated F-pSi loaded with DiI; (D) J771A.1 after 10 min incubation with NF-pSi loaded with DiI; (E) J774a.1 after 1 h incubation with Lysotracker Red and 10 min incubation with NF-pSi with calcein; (F) J774a.1 after 5 min incubation with MTP-FAM conjugated NF2-pSi loaded with DiI. (G-I) Transmission electron microscopy (TEM) of HeLa cells after 1 h incubation with particles; (G) Non-fusogenic liposome-coated particles localized in vesicles (endosome/lysosome). Inset shows pinocytotic uptake of particles. Scale bar indicates 1 μm; (H) Fusogenic liposome-coated particles localized in cell cytoplasm. Scale bar indicates 500 nm; and (I) Fusogenic liposome-coated particles localized in cell cytoplasm. Scale bar indicates 1 μm.

FIG. 5A-B shows confocal microscopy of Neuro2a cells after 1 h incubation with particles; (A) Fusogenic liposomes showed DiI signals in the cell membrane, indicating fusogenic uptake; (B) Non-fusogenic liposomes showed DiI signal in the cell cytoplasm in distinct concentrated spots, indicating endocytic uptake.

FIG. 12 shows confocal microscopy of Neuro2a and HeLa cells after incubation with particles; Top left panel: Neuro2a cells after 1 h incubation with fusogenic liposome-coated particles loaded with lipophilic fluorescent dye, DiI; Top right panel: HeLa cells after 8 h incubation with fusogenic liposome-coated particles loaded with cell impermeable dye, Calcein; Bottom left panel: Neuro2a cells after 1 h incubation with non-fusogenic liposome-coated particles loaded with lipophilic fluorescent dye, DiI; Bottom right panel: HeLa cells after 8 h incubation with non-fusogenic liposome-coated particles loaded with cell impermeable dye, Calcein.

FIG. 13A-B shows Confocal microscopy of Neuro2a cells after 1 h incubation with particles; (A) RVG-conjugated fusogenic liposomes (RVG-F) show successful RVG targeting to cells and high level of fusion staining; (B) Fusogenic liposomes (F) without RVG conjugation show fusion at a relatively lower level compared to RVG-conjugated particles.

FIG. 15A-K shows FACS analyses of calcein accumulation in homogenized *Staph. aureus* infected Balb/C lungs. (A) PBS vs. NF-pSi loaded with calcein (Cal) and conjugated to targeting peptide (MTP); (B) PBS vs. F-pSi loaded with calcein without targeting peptide. (C) PBS vs. F-pSi loaded with calcein and conjugated to MTP. (D-K) unstained healthy or infected lung histology sections imaged for fluorescence detection of DiI-loaded particles.

DETAILED DESCRIPTION

Figure 1A:
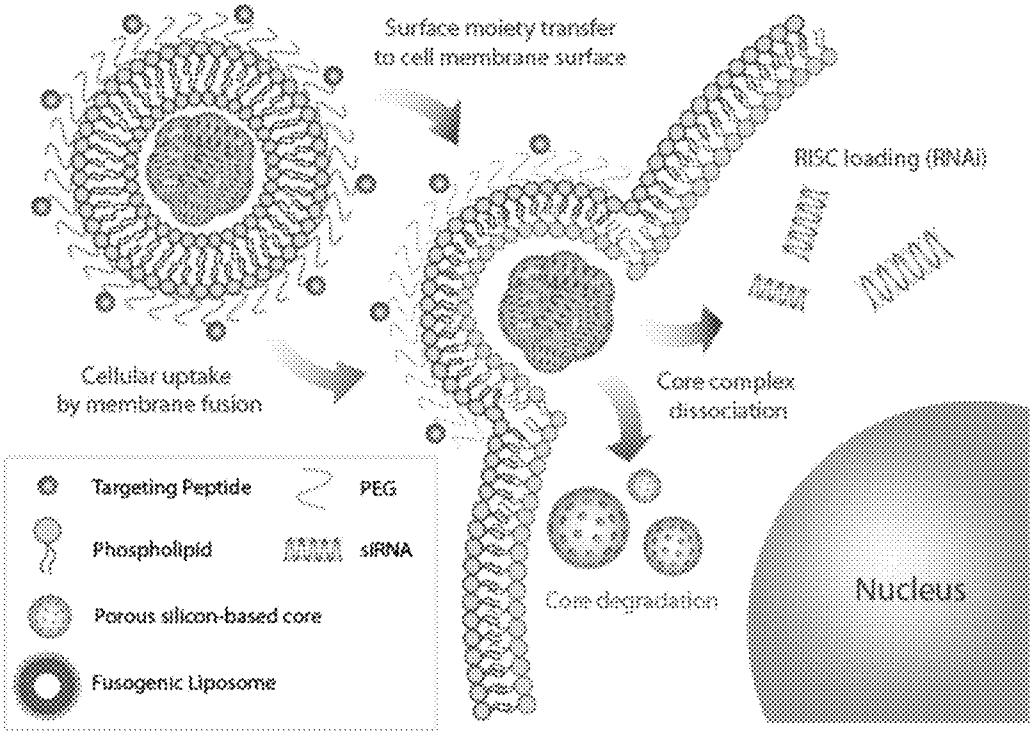

As used herein and in the appended claims, the singular forms "a," "and," and "the" include plural referents unless the context clearly dictates otherwise. Thus, for example, reference to "a pore" includes a plurality of such pores and reference to "the antigen" includes reference to one or more antigens known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Gene delivery systems for in vivo therapeutics remain a challenge due to low efficiency or cytotoxicity. Cellular endocytosis is the primary uptake pathway of most nano-platforms, which results in lysosomal degradation of genetic material and low therapeutic efficacy.

Porous silicon and silicon oxide have been investigated as candidate drug delivery vehicle materials in many applications for their inorganic and biodegradable nature. The porous nanostructures can hold therapeutics, diagnostic agents, or other beneficial substances (sometimes referred to herein as "payloads"). However, premature release of these payloads, either prior to or post-administration, can be undesirable for the intended purpose. Additionally, the degradation of porous silicon or porous silicon oxide in aqueous conditions at sites other than the target site has posed a significant problem for sustained drug delivery, in vivo or in vitro imaging, and biosensor applications, which can benefit from protective coating around the porous silicon core.

Lipid-based nanoparticles were first Food and Drug Administration (FDA)-approved three decades ago in the form of Doxil®, doxorubicin-encapsulating liposome. Liposomal formulation of vincristine sulfate for acute lymphoblastic leukemia, Marquibo®, was approved as recently as 2012, and several paclitaxel and cisplatin formulations such as EndoTag-1 and SPI-077 are in clinical trials. The reason for such continuous investment in liposomal formulations is attributed to their major advantages: biocompatibility, ease of synthesis, and surface modifiability.

Lipid nanoparticles have difficulty in delivering genetic material due to low loading efficiency and high rate of lysosomal degradation. Small interfering RNA (siRNA)-loaded lipid nanoparticles are taken up by cells through clathrin-mediated endocytosis and macro/micropinocytosis with proton pump, mTOR, and cathepsin activations. After the uptake, approximately 70% of the internalized siRNA are exocytosed out of the cell after lipids comprising the nanoparticles are recycled at late endosome/lysosome stages through Niemann-Pick type Cl (NPC1) regulation. Only 1-2% of the siRNA are able to escape from the early endosome into the cytosol. Therefore, a delivery system that bypasses the lipid recycling in late endosome/lysosome is vital in achieving high therapeutic efficacy.

The preparation of nano-, micro-, meso-, and macroporous silicon by electrochemical or chemical means is well established, as is the conversion of the material to the corresponding nano-, micro-, meso-, and macroporous silicon oxide, either partially or completely. Moreover, liposomes are known and recognized in the art The disclosure provides a biodegradable liposomal porous silicon (pSi) nanoparticle system that can bypass endocytic uptake via liposome-plasma membrane fusion (see, e.g., FIG. 1A). Membrane fusion allows a direct release of hydrophilic payloads from the core of liposomes into the cell cytoplasm, as well as a transfer of hydrophobic molecules from the liposomal bilayer to the cell membrane bilayer. In addition, the liposomal porous silicon nanoparticle system allows a transfer of moieties conjugated on the outer surface of liposomes (antibodies, small molecules, peptides, etc.) to the cell membrane surface. The porous silicon core has photoluminescence properties that allows for these particles to be used as a tracking tool using time-gated luminescence imaging. Moreover, the porous silicon allows for condensation of the highly anionic genetic material into small clusters, allowing liposomes to easily encapsulate the particle and any payloads contained in the pores of the particle. The disclosure demonstrates that fusogenic liposomal-coated pSi particles fuse with the membrane of cells and transfer various payloads into the cell. For example, the disclosure demonstrates that the fusogenic liposomal-coated pSi particles successfully fuse with Neuro2a mouse neuroblast cells, and transfers lipophilic DiI dye from the liposomal membrane to the cellular membrane. In contrast, non-fusogenic pSi particles were found in the cells in small groups indicative of endosomal uptake and lysosomal localization. Additionally, surface conjugation of Neuro2a-targeting moiety, rabies virus glycoprotein (RVG), allowed an accelerated rate of fusion of the liposomal pSi. Overall, the liposomal porous silicon nanoparticles demonstrate potential as a highly effective delivery vehicle.

As used herein the term "microparticle" or "nanoparticle", "micro- and/or nanoparticle", "LPSiNP" and "pSiNP" refers to a porous silicon material at least partially comprising silicon dioxide and which have a size range of a few nanometers to hundred micrometers. Typically the size is about 10-20 nm to 1 micrometer. The geometry of the porous silicon material/particles may be spherical, oblong, square, rectangular, cuboidal and the like.

It should be understood that here "porous silicon oxide" refers to a substance containing silicon and oxygen of general stoichiometric formula $SiO_x$, where x can be as small as 0.01 and as large as 2, and that "porous silicon" refers to a substance that is composed of elemental silicon (either in its crystalline or amorphous state), with a surface containing hydrogen, oxygen, or carbon-containing species. Here the terms "porous silicon" or "porous silicon oxide" refer to materials containing micropores (pore sizes typically smaller than about 2 nm), mesopores (pore size typically in the range about 2-50 nm), or macropores (pore sizes larger than about 50 nm), or combinations of any two or all three pore types. Further it should be understood that the surface of the porous materials, including the surface of the inner pore walls, may contain hydrogen, oxygen, or carbon-containing species.

The disclosure provides porous silicon micro- and/or nanoparticles (pSiNP) that can carry one or more molecule to be delivered to a cell or tissue. The molecules can be diagnostic and/or therapeutic. In some embodiments, the molecules are anti-cancer agents, anti-inflammatory agents, small molecule drugs, peptides, polypeptides, nucleic acids (e.g., siRNA) and the like.

Furthermore, in contrast to many micro- and nanomaterials (e.g., carbon nanotubes (CNT), gold nanoparticles (GN), and quantum dots (QD)), pSiNP degrade into renally cleared components in a relatively short period of time with little or no evidence of toxicity. Additionally, in contrast to many biologic-derived delivery systems, the nanoparticles alone (without an added activating complex or molecule) do not induce an immune response.

The porous silicon micro- and/or nano-particles containing a desired payload (e.g., nucleic acids, peptides, small molecules etc.) can be encapsulated into a liposome (fusogenic or non-fusogenic). The liposome can be modified to be target specific or can be unmodified (see, e.g., FIG. 1).

Accordingly, the disclosure provides a biodegradable porous micro- and/or nanostructure comprising silicon material encapsulated in a liposomal vesicle. In one embodiment, the silicon material comprises a silicon dioxide material. In another embodiment, the silicon material comprises both a silicon and a silicon dioxide material. In another embodiment, the biodegradable/biocompatible porous nanostructure comprises a particulate size of between about 0.01 μm and 1 μm. In yet another embodiment, the biodegradable/biocompatible porous structure can be characterized as non-toxic. In yet another embodiment, the porous silicon material is loaded with a "payload" material. The payload material can be a drug, small molecule, diagnostic agent, therapeutic agent, peptide, antibody, antibody fragment, polypeptide, nucleic acid (e.g., siRNA) and the like.

The disclosure also provides a method of preparing porous silicon particles comprising (1) electrochemically etching a silicon wafer to generate a porous structured film; (2) lifting off said porous structured film from the silicon wafer substrate; (3) fracturing the porous film to generate micro- and/or nanoparticles of sizes between 10 nanometers and 1000 nanometers; and (4) activating the structure in an aqueous solution. In one embodiment, the aqueous solution comprises pure water. In one embodiment, the aqueous solution comprises sodium hydroxide, hydrogen peroxide or borate.

For example, porous silicon nanoparticles (pSiNPs) can be prepared as describe by Qin et al. (Part. Part. Syst. Charact. 31(2):252-256, 2014; the disclosure of which is incorporated herein by reference). Briefly, porous silicon is prepared by galvanostatic anodic etch of crystalline silicon wafers. Perforations along the etched planes are introduced by short periodic pulses of high current during a long low-current etch, generating layers of alternating high and low porosity. The layer of porous silicon is removed from the wafer by applying low current density pulse in dilute aqueous HF, and the resulting freestanding films are fractured by ultrasonication. This results in porous nanoparticles of predetermined porosity and average pore size. The tunability of porosity and pore size is useful in determining the efficiency of the subsequent payload loading process.

Figure 1B:
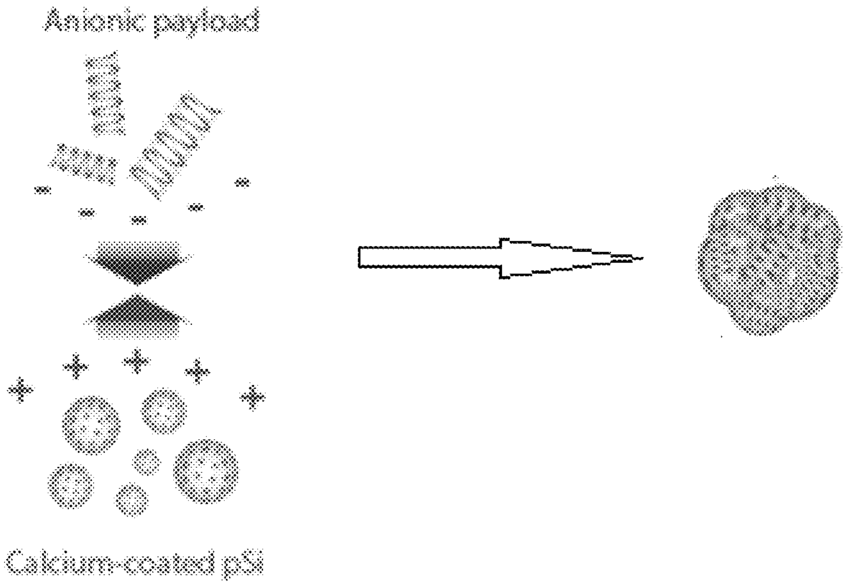
Figure 2:
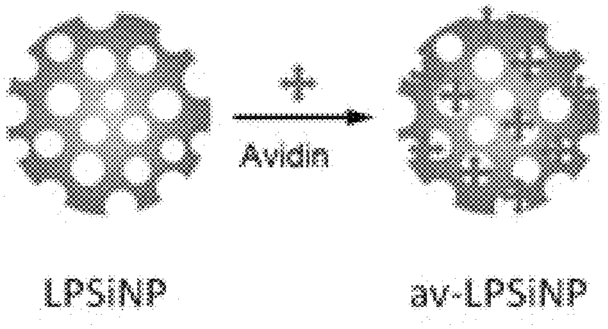
FIG. 2 shows a schematic of drug loading of porous silicon nanoparticles.
Figure 3:
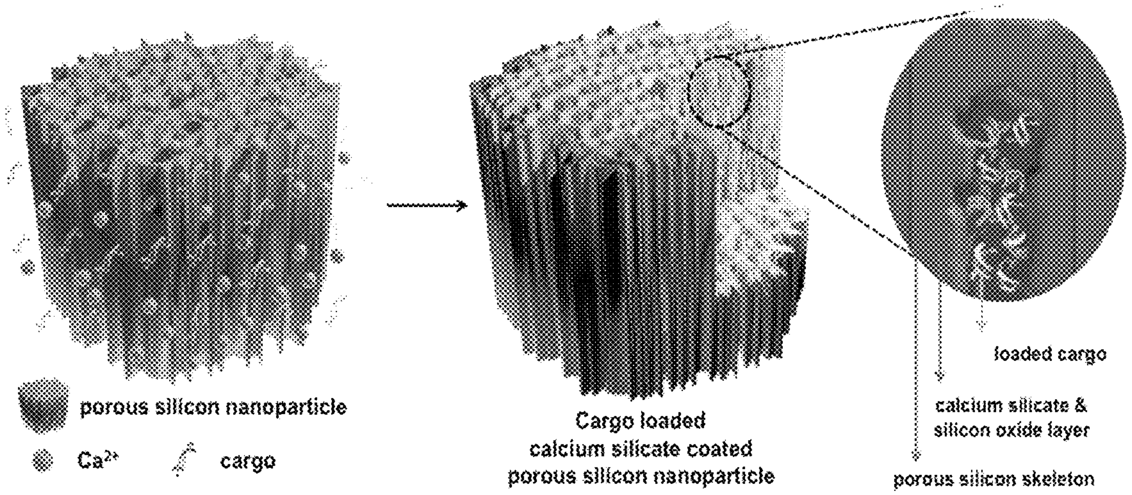
FIG. 3 shows a schematic of cargo-loaded calcium silicate-coated porous silicon nanoparticles (Ca-pSiNP).

In embodiments with payloads, the porous silicon particles can be placed in an aqueous solution containing the payload and 1M or greater concentration of, for example, calcium chloride ($CaCl_2$) solution. The solution is mixed and purified by centrifugation, resulting in cargo-loaded calcium silicate coated porous silicon nanoparticle (Ca-pSiNP-cargo). As a control. Calcium silicate coated porous silicon nanoparticles without payload (Ca-pSiNP) can be prepared in the same manner as described above, but excluding the added payload solution. FIG. 1B, 2-3 illustrates the cargo-loaded calcium silicate-coated porous silicon nanoparticle.

It will be apparent to those skilled in the art that other embodiments may be used to generate Ca-pSiNP, one example involving substituting a chemical stain etch for the electrochemical etch used to produce the porous silicon core, and the other utilizing a porous silicon core prepared by chemical reduction of a nanostructured silicon oxide. Stain etching uses silicon powder instead of silicon wafers as silicon precursor, and a chemical oxidant instead of electrical power supply to drive the electrochemical reaction. In some cases, it may be desirable to substitute calcium nitrate, calcium nitrite, calcium gluconate, or other calcium ion sources for calcium chloride. Calcium nitrate or calcium nitrite can oxidize porous silicon more quickly than calcium chloride due to the oxidizing nature of the nitrate and nitrite ions.

In one embodiment, the porous silicon particles can be luminescent. The disclosure provides a method of generating luminescent porous Si nanoparticles (LPSiNP). The method comprises electrochemical etching of a p-type silicon wafer by application of a constant current density of about 200 $mA/cm^2$ in an aqueous HF/ethanol electrolyte. The resulting freestanding film of porous silicon nanostructure is then removed from the crystalline silicon substrate by application of a current pulse of about 4 $mA/cm^2$ in an aqueous HF/ethanol electrolyte. The freestanding hydrogen-terminated porous silicon film is subsequently fractured, e.g., by sonication, and then filtered to obtain a desired particle size. Other methods of size selecting the nanoparticles can be performed by centrifugation and chromatography. The nanoparticles are further incubated in deionized (DI) water or other oxidizing aqueous environment such as, for example, a borate aqueous buffer, to activate their luminescence (e.g., in one embodiment in the near-infrared range). Various aqueous buffers that are oxidizing (or neutral to basic) can be used. In some embodiments, an aqueous buffer selected from the group consisting of an aqueous borate buffer, a phosphate buffered saline, and sodium hydroxide. For example, in one embodiment, a borate aqueous buffer is useful. The resulting LPSiNP can then be further modified or loaded with a desired drug agent or other factor. The loaded or modified LPSiNP's can then be encapsulated by/into a liposome.

In another embodiment, the LPSiNP materials can be generated by first producing a silicon layer with a pore size range of 2-100 nm (e.g., 5-10 nm, 10-20 nm, 20-30 nm etc.). The silicon layer is etched into the single-crystal silicon substrate in ethanolic HF solution. The entire porous nanostructure is removed from the Si substrate by application of a current pulse. The freestanding hydrogen-terminated porous silicon film is then placed in an aqueous solution and fractured into multi-sized particles by, for example, overnight ultrasonication. The particles can then be filtered if desired (e.g., through a 0.22 μm porous filtration membrane or other size separating device) to obtain porous silicon nanoparticles. For example, separation or size control of LPSiNPs can be achieved by passing the colloidal suspension through physical filters, by centrifugation of the suspension, by electrophoresis, by size exclusion chromatography, or by electrostatic precipitation. The nanoparticles are incubated in an aqueous oxidizing solution to activate their luminescence.

The activation of luminescence is performed in an aqueous solution. During the activation silicon oxide grows on the hydrogen-terminated porous silicon surface, generating significant luminescence attributed to quantum confinement effects and to defects localized at the Si/$SiO_2$ interface. The preparation conditions of the nanoparticles can be optimized to provide pore volumes and surface areas suitable for loading of therapeutics and for desired in vivo circulation times while maintaining an acceptable degradation rate.

The thickness, pore size, and porosity of a given film is controlled by the current density, duration of the etch cycle, and etchant solution composition. In addition, a porous silicon film can be used as a template to generate an imprint of biologically compatible or bioresorbable materials. The porous silicon film or its imprint possess a sinusoidally varying porosity gradient, providing sharp features in the optical reflectivity spectrum that can be used to monitor the presence or absence of chemicals trapped in the pores.

For in vivo applications, it is often desirable to prepare porous Si in the form of particles. The porous layer can be removed from the Si substrate with a procedure commonly referred to as "electropolishing" or "lift-off." The etching electrolyte is replaced with one containing a lower concentration of HF and a current pulse is applied for several seconds. The lower concentration of HF results in a diffusion limited situation that removes silicon from the crystalline Si/porous Si interface faster than pores can propagate. The result is an undercutting of the porous layer, releasing it from the Si substrate. The freestanding porous Si film can then be removed with tweezers or a vigorous rinse. The film can then be converted into microparticles by ultrasonic fracture. Conventional lithography or microdroplet patterning methods can also be used if particles with more uniform shapes are desired.

The ability to easily tune the pore sizes and volumes during the electrochemical etch is a unique property of porous Si that is very useful for drug delivery applications. Other porous materials generally require a more complicated design protocol to control pore size, and even then, the available pore sizes tend to span a limited range. With electrochemically prepared porous Si, control over porosity and pore size is obtained by adjusting the current settings during etching. Typically, larger current density produces larger pores. Large pores are desirable when incorporating sizable molecules or drugs within the pores. Pore size and porosity is important not only for drug loading; it also determines degradation rates of the porous Si host matrix.

Smaller pores provide more surface area and expose more sites for attack of aqueous media. The smaller porous filaments within the film yield greater dissolution rates, providing a convenient means to control degradation rates of the porous Si host.

With its high surface area, porous Si is particularly susceptible to air or water oxidation. Once oxidized, nanophase $SiO_2$ readily dissolves in aqueous media, and surfactants or nucleophiles accelerate the process. Si—O bonds are easy to prepare on porous Si by oxidation, and a variety of chemical or electrochemical oxidants can be used. Thermal oxidation in air tends to produce a relatively stable oxide, in particular if the reaction is performed at >600° C. Ozone oxidation, usually performed at room temperature, forms a more hydrated oxide that dissolves quickly in aqueous media.

Slow oxidation of the porous Si surface by dimethyl sulfoxide (DMSO), when coupled with dissolution of the newly formed oxide by HF, is a mild means to enlarge the pores in porous Si films. Aqueous solutions of bases such as KOH can also be used to enlarge the pores after etching. Electrochemical oxidation, in which a porous Si sample is anodized in the presence of a mineral acid such as $H_2SO_4$, yields a fairly stable oxide. Oxidation imparts hydrophilicity to the porous structure, enabling the incorporation and adsorption of hydrophilic drugs or biomolecules within the pores. Aqueous oxidation in the presence of various ions including $Ca^{2+}$ generates a calcified form of porous Si that has been shown to be bioactive and is of particular interest for in vivo applications. Calcification can be enhanced by application of a DC electric current.

The fusogenic liposome-coated nanoparticles of the disclosure provide a device and method for drug delivery and tissue and disease (e.g., tumor) monitoring. A drug-delivery fusogenic liposome-coated nanoparticles composition can include any number of candidate drugs depending upon the type of condition, tissue, or cancer to be treated. A candidate drug may be "physically" trapped within the pores of the silicon particle, or, the pores themselves may be chemically modified to bind the candidate drug. Such a drug can include in the general sense a peptide, polypeptide, small molecule agent, nucleic acid and combinations thereof.

More specifically, "physical trapping" is similar to building a ship in a bottle, where the "ship" is the candidate drug and the "bottle" is the nanometer-scale pores in the porous Si particle. Small molecules can be trapped in the porous matrix by oxidizing the porous Si around the molecule. Since oxidation of silicon adds two atoms of oxygen per atom of Si to the material, there is a significant increase in volume of the matrix upon oxidation. This has the effect of swelling the pore walls and shrinking the free volume inside the pores, and under the appropriate conditions, molecules present in the pores during oxidation become trapped in the oxide matrix. One embodiment of the trapping process is the increased concentration of the active ingredient which occurs during the trapping process. The crystals may present a negatively charged environment and an active ingredient, such as proteins and other drugs, may be concentrated in the crystals to levels much higher than the free concentration of the active ingredient in solution. This can result in 10 to 100 fold or more increase in active ingredient concentration when associated with a crystal. The oxidizing can be performed at repeated intervals by performing layered oxidation. For example, a biological agent or drug can be trapped in the pores by controlled addition of oxidants. Oxidation of the freshly prepared (hydride-terminated) porous Si material results in an effective shrinking of the pores. This occurs because the silicon oxide formed has a larger volume than the Si starting material. If a drug is also present in the solution that contains the oxidant, the drug becomes trapped in the pores. Furthermore the porous silicon oxide can comprise a higher concentration of a biological agent or drug than a non-oxidized Si hydride material.

The free volume in a porous Si film is typically between 50 and 80%. Oxidation should reduce this value somewhat, but the free volume is expected to remain quite high. Most of the current drug delivery materials are dense solids and can deliver a small percentage of drug by weight.

Various approaches to load a molecular payload into a porous Si host have been explored, and they can be grouped into the following general categories: covalent attachment, physical trapping, and adsorption.

Covalent attachment provides a convenient means to link a biomolecular capture probe to the inner pore walls of porous Si for biosensor applications, and this approach can also be used to attach drug molecules, peptides and the like. As described elsewhere herein, linking a biomolecule via Si—C bonds tends to be a more stable route than using Si—O bonds due to the susceptibility of the Si—O species to nucleophilic attack.

One of the more common approaches is to graft an organic molecule that contains a carboxyl species on the distal end of a terminal alkene. The alkene end participates in the hydrosilylation reaction, bonding to the Si surface and leaving the carboxy-terminus free for further chemical modification. One such linker molecule is undecylenic acid, which provides a hydrophobic 10 carbon aliphatic chain to insulate the linker from the porous Si surface. The drug payload can be attached directly to the carboxy group of the alkene, or it can be further separated from the surface with a PEG linker. Due to the stability of the Si—C bond, hydrosilylation is good way of attaching a payload to porous Si. The payload is only released when the covalent bonds are broken or the supporting porous Si matrix is degraded.

In yet another embodiment, electrostatic adsorption can be used, essentially an ion exchange mechanism that holds molecules more weakly. Electrostatics is a useful means to affect more rapid drug delivery, as opposed to covalent or physical trapping approaches that release drug over a period of days, weeks, or months.

The affinity of a porous Si particle for a particular molecule can be controlled with surface chemistry. The surface of oxidized porous Si has a point of zero charge at a pH of around 2, and so it presents a negatively charged surface to most aqueous solutions of interest. At the appropriate pH, porous $SiO_2$ spontaneously adsorbs positively charged proteins such as serum albumin, fibrinogen, protein A, immunoglobulin G (IgG), or horseradish peroxidase, concentrating them in the process.

A calcium silicate porous silicon core is useful for providing a dual role of condensing the anionic genetic payload with high loading efficiency, and of emitting photoluminescence to allow for particle tracking. The calcium silicate is cationic, which allows for strong electrostatic interactions with the anionic nucleotides to form a stable cluster of genes and particles. Another aspect of the calcium silicate pSiNPs is the quick dispersion and degradation in intercellular environment when the liposomal coating is shed by membrane fusion upon uptake; delayed separation or degradation of the condenser from the nucleotide payloads can result in excretion of the entire cluster, as the cell recognizes the foreign materials to be inoperable. Data has demonstrated that fusogenic particles containing a core calcium silicate pSi quickly degrades and lose photoluminescence without the liposomal protection in the cell cytoplasm. On the other hand, the non-fusogenic particles remain intact within endosomes and lysosome, to retain the pSi photoluminescence. The quick degradation of calcium silicate pSiNPs allows for release of, e.g., siRNA into the cytoplasm to undergo RNA interference and gene silencing.

Porous Si can also be made hydrophobic, and hydrophobic molecules such as the steroid dexamethasone or serum albumin can be loaded into these nanostructures. Hydrophilic molecules can also be loaded into such materials with the aid of the appropriate surfactant. The native hydride surface of porous Si is hydrophobic. Such techniques have been used for short-term loading and release. Because water is excluded from these hydrophobic surfaces, aqueous degradation and leaching reactions tend to be slow. The grafting of alkanes to the surface by hydrosilylation is commonly used to prepare materials that are stable in biological media; this stability derives in large part from the ability of the hydrophobic moieties to locally exclude water or dissolved nucleophiles.

Other drugs (e.g., cargo) or "active ingredient" that can be used with the porous silicon particles of the disclosure include any one or any combination of the following, but are not limited to, anti-angiogenic compounds such as bevacizumab, ranibizumab, pegaptanib, and other compounds in the angiogenic cascade. Anti-cancer drugs such as, for example, chemotherapeutic compounds and/or derivatives thereof (e.g., 5-fluorouracil, vincristine, vinblastine, cisplatin, doxyrubicin, adriamycin, tamocifen, etc.). Also included are glucocorticosteroids such as dexamethasone, triamcinolone acetonide, fluocinolone acetonide and other comparable compounds in the corticosteroid and cortisene families. Also included are compounds such as antacids, anti-inflammatory substances, coronary dilators, cerebral dilators, peripheral vasodilators, anti-infectives, psychotropics, anti-manics, stimulants, anti-histamines, laxatives, decongestants, vitamins, gastrointestinal sedatives, anti-diarrheal preparations, anti-anginal drugs, vasodilators, anti-arrhythmics, anti-hypertensive drugs, vasoconstrictors and migraine treatments, anti-coagulants and anti-thrombotic drugs, analgesics, anti-pyretics, hypnotics, sedatives, anti-emetics, anti-nauseants, anti-convulsants, neuromuscular drugs, hyper- and hypoglycemic agents, thyroid and anti-thyroid preparations, diuretics, anti-spasmodics, uterine relaxants, mineral and nutritional additives, anti-obesity drugs, anabolic drugs, erythropoietic drugs, anti-asthmatics, bronchodilators, expectorants, cough suppressants, mucolytics, drugs affecting calcification and bone turnover and anti-uricemic drugs. Specific drugs include gastro-intestinal sedatives such as metoclopramide and propantheline bromide; antacids such as aluminum trisilicate, aluminum hydroxide, ranitidine and cimetidine; anti-inflammatory drugs such as phenylbutazone, indomethacin, naproxen, ibuprofen, flurbiprofen, diclofenac, dexamethasone, prednisone and prednisolone; coronary vasodilator drugs such as glyceryl trinitrate, isosorbide dinitrate and pentaerythritol tetranitrate; peripheral and cerebral vasodilators such as soloctidilum, vincamine, naftidrofuryl oxalate, co-dergocrine mesylate, cyclandelate, papaverine and nicotinic acid; anti-infective substances such as erythromycin stearate, cephalexin, nalidixic acid, tetracycline hydrochloride, ampicillin, flucloxacillin sodium, hexamine mandelate and hexamine hippurate; neuroleptic drugs such as flurazepam, diazepam, temazepam, amitryptyline, doxepin, lithium carbonate, lithium sulfate, chlorpromazine, thioridazine, trifluperazine, fluphenazine, piperothiazine, haloperidol, maprotiline hydrochloride, imipramine and desmethylimipramine; central nervous stimulants such as methylphenidate, ephedrine, epinephrine, isoproterenol, amphetamine sulfate and amphetamine hydrochloride; antihistamic drugs such as diphenhydramine, diphenylpyraline, chlorpheniramine and brompheniramine; anti-diarrheal drugs such as bisacodyl and magnesium hydroxide; the laxative drug, dioctyl sodium sulfosuccinate; nutritional supplements such as ascorbic acid, alpha tocopherol, thiamine and pyridoxine; anti-spasmodic drugs such as dicyclomine and diphenoxylate; drugs affecting the rhythm of the heart such as verapamil, nifedipine, diltiazem, procainamide, disopyramide, bretylium tosylate, quinidine sulfate and quinidine gluconate; drugs used in the treatment of hypertension such as propranolol hydrochloride, guanethidine monosulphate, methyldopa, oxprenolol hydrochloride, captopril and hydralazine; drugs used in the treatment of migraine such as ergotamine; drugs affecting coagulability of blood such as epsilon aminocaproic acid and protamine sulfate; analgesic drugs such as acetylsalicylic acid, acetaminophen, codeine phosphate, codeine sulfate, oxycodone, dihydrocodeine tartrate, oxycodeinone, morphine, heroin, nalbuphine, butorphanol tartrate, pentazocine hydrochloride, cyclazacine, pethidine, buprenorphine, scopolamine and mefenamic acid; anti-epileptic drugs such as phenytoin sodium and sodium valproate; neuromuscular drugs such as dantrolene sodium; substances used in the treatment of diabetes such as tolbutamide, disbenase glucagon and insulin; drugs used in the treatment of thyroid gland dysfunction such as triiodothyronine, thyroxine and propylthiouracil, diuretic drugs such as furosemide, chlorthalidone, hydrochlorthiazide, spironolactone and triamterene; the uterine relaxant drug ritodrine; appetite suppressants such as fenfluramine hydrochloride, phentermine and diethylproprion hydrochloride; anti-asthmatic and bronchodilator drugs such as aminophylline, theophylline, salbutamol, orciprenaline sulphate and terbutaline sulphate; expectorant drugs such as guaiphenesin; cough suppressants such as dextromethorphan and noscapine; mucolytic drugs such as carbocisteine; anti-septics such as cetylpyridinium chloride, tyrothricin and chlorhexidine; decongestant drugs such as phenylpropanolamine and pseudoephedrine; hypnotic drugs such as dichloralphenazone and nitrazepam; anti-nauseant drugs such as promethazine theoclate; haemopoietic drugs such as ferrous sulphate, folic acid and calcium gluconate; uricosuric drugs such as sulphinpyrazone, allopurinol and probenecid; and calcification affecting agents such as biphosphonates, e.g., etidronate, pamidronate, alendronate, residronate, teludronate, clodronate and alondronate.

Insofar as the disclosure contemplates including a virtually unlimited number of drugs, in vitro pharmacokinetic studies can be used to determine the appropriate configuration of the porous silicon particles for each drug. The drug-conjugated silicon particles can be monitored once delivered to a subject. For example, light intensity from luminescent silicon nanoparticles (LPSiNPs) can be measured using a low power spectrophotometer. Using such methods the half-life, delivery and collection of drugs and/or LPSiNPs can be monitored.

The luminescent spectrum used in particle identification can readily be measured with inexpensive and portable instrumentation such as a CCD spectrometer or a diode laser interferometer. Removal of a drug from the LPSiNPs can result in a change in the luminescence of the LPSiNPs as a wavelength shift in the spectrum. Such techniques can be used to enable non-invasive sensing through opaque tissue.

In any of the foregoing embodiments, the silicon particle carrying cargo (e.g., loaded or bound to a drug or agent) or free of any agent and/or wherein the particles are luminescent or non-luminescent are encapsulated in a liposome suitable for fusion with a cell membrane (e.g., fusogenic liposomes). Moreover, these liposomes may be modified or unmodified. If modified, the modification can include a targeting moiety as described further herein.

Fusogenic liposome formulations can be prepared from any number of known lipids. The liposomal vesicle can be made from a plurality of lipids, wherein the liposomes have a diameter between 10 and 500 nm or any diameter there between (e.g., 20-400, 50-300, 60-250, 100-200, 120-180, 140-160 nm etc.). In a further embodiment, the liposomes are unilamellar liposomes or micelles. In another embodiment, the liposomes are multilamellar liposomes. In another embodiment, the plurality of lipids comprise phospholipids selected from phosphatidylcholine, phosphatidic acid, phosphatidylethanolamine, phosphatidylglycerol, phosphatidylserine, lysophosphatidylcholine, and/or any derivative thereof. In yet another embodiment, the phospholipid derivatives are selected from 1,2-di-(3,7,11,15-tetramethylhexadecanoyl)-sn-glycero-3-phosphocholine, 1,2-didecanoyl-sn-glycero-3-phosphocholine, 1,2-dierucoyl-sn-glycero-3-phosphate, 1,2-dierucoyl-sn-glycero-3-phosphocholine, 1,2-dierucoyl-sn-glycero-3-phosphoethanolamine, 1,2-dilinoleoyl-sn-glycero-3-phosphocholine, 1,2-dilauroyl-sn-glycero-3-phosphate, 1,2-dilauroyl-sn-glycero-3-phosphocholine, 1,2-dilauroyl-sn-glycero-3-phosphoethanolamine, 1,2-dilauroyl-sn-glycero-3-phospho-(1'-rac-glycerol), 1,2-dimyristoyl-sn-glycero-3-phosphate, 1,2-dimyristoyl-sn-glycero-3-phosphocholine, 1,2-dimyristoyl-sn-glycero-3-phosphoethanolamine, 1,2-dimyristoyl-sn-glycero-3-phosphoglycerol, 1,2-dimyristoyl-sn-glycero-3-phosphoserine, 1,2-dioleoyl-sn-glycero-3-phosphate, 1,2-dioleoyl-sn-glycero-3-phosphocholine, 1,2-dioleoyl-sn-glycero-3-phosphoethanolamine, L-alpha-phosphatidyl-DL-glycerol, 1,2-dioleoyl-sn-glycero-3-phosphoserine, 1,2-dipalmitoyl-sn-glycero-3-phosphate, 1,2-dipalmitoyl-sn-glycero-3-phosphocholine, 1,2-dipalmitoyl-sn-glycero-3-phosphoethanolamine, 1,2-dipalmitoyl-sn-glycero-3-phosphoglycerol, 1,2-dipalmitoyl-sn-glycero-3-phosphoserine, 1,2-distearoyl-sn-glycero-3-phosphate, 1,2-distearoyl-sn-glycero-3-phosphocholine, 1,2-distearoyl-sn-glycero-3-phosphoethanolamine, 1,2-distearoyl-sn-glycero-3-phosphoglycerol, egg sphingomyelin, egg-PC, hydrogenated Egg PC, hydrogenated Soy PC, 1-myristoyl-sn-glycero-3-phosphocholine, 1-palmitoyl-sn-glycero-3-phosphocholine, 1-stearoyl-sn-glycero-3-phosphocholine, 1-myristoyl-2-palmitoyl-sn-glycero 3-phosphocholine, 1-myristoyl-2-stearoyl-sn-glycero-3-phosphocholine, 1-palmitoyl-2-myristoyl-sn-glycero-3-phosphocholine, 1-palmitoyl-2-oleoyl-sn-glycero-3-phosphocholine, 1-palmitoyl-2-oleoyl-sn-glycero-3-phosphoethanolamine, 1-palmitoyl-2-oleoyl-sn-glycero-3-phosphoglycerol, 1-palmitoyl-2-stearoyl-sn-glycero-3-phosphocholine, 1-stearoyl-2-myristoyl-sn-glycero-3-phosphocholine, 1-stearoyl-2-oleoyl-sn-glycero-3-phosphocholine, and/or 1-stearoyl-2-palmitoyl-sn-glycero-3-phosphocholine. In a further embodiment, the liposomes further comprise cholesterol. In yet another embodiment, the liposomes further comprise polyethylene glycol. For example, in one embodiment, the fusogenic liposomal formulation can be prepared from 1,2-dimyristoyl-sn-glycero-3-phosphocholine (DMPC), 1,2-distearoyl-sn-glycero-3-phosphoethanolamine-N-[methoxy(polyethylene glycol)-2000](DSPE-PEG), and 1,2-dioleoyl-3-trimethylammonium-propane (DOTAP) in molar ratio of 76.2:3.8:20. For experimental controls, non-fusogenic formulations can be synthesized in the same manner, but at molar ratio of 80:0:20 (i.e., lacking PEG). DSPE-PEG (methoxy) may be replaced in the same molar ratio with carboxylic acid—(DSPE-PEG (carboxy)) or maleimide—(DSPE-PEG (maleimide)) functionalized PEG lipid for further surface modifications such as with targeting moieties. For example, use of DSPE-PEG (carboxy) or DSPE-PEG (meleimide) are useful for modification with antibodies or targeting peptides, respectively. In another embodiment, the liposomes further comprise one or more site-targeting moieties. Examples of site-targeting moieties include, but are not limited to, peptides, aptamers, antibodies, and antibody fragments (e.g., $F(ab')_2$, Fab, and scFv).

The term "lipid" refers to any suitable material resulting in a bilayer such that a hydrophobic portion of the lipid material orients toward the bilayer while a hydrophilic portion orients toward the aqueous phase. Amphipathic lipids are used as the primary lipid vesicle structural element. Hydrophilic characteristics derive from the presence of phosphato, carboxylic, sulfato, amino, sulfhydryl, nitro, and other like groups. Hydrophobicity can be conferred by the inclusion of groups that include, but are not limited to, long chain saturated and unsaturated aliphatic hydrocarbon groups and such groups substituted by one or more aromatic, cycloaliphatic or heterocyclic group(s). Typical amphipathic compounds are phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine could be used. Other compounds lacking in phosphorus, such as sphingolipid and glycosphingolipid families are also within the group designated as lipid. Additionally, the amphipathic lipids described above may be mixed with other lipids including triglycerides and sterols.

The term "neutral lipid" refers to any of a number of lipid species which exist either in an uncharged or neutral zwitterionic form at physiological pH. Such lipids include, for example diacylphosphatidylcholine, diacylphosphatidylethanolamine, ceramide, sphingomyelin, cephalin, and cerebrosides.

The term "non-cationic lipid" refers to any neutral lipid as described above as well as anionic lipids. Examples of anionic lipids include cardiolipin, diacylphosphatidylserine and diacylphosphatidic acid.

The term "cationic lipid" refers to any of a number of lipid species which carry a net positive charge at physiological pH. Such lipids include, but are not limited to, DODAC, DOTMA, DDAB, DOTAP, DC-Chol and DMRIE. Additionally, a number of commercial preparations of cationic lipids are available which can be used in the disclosure. These carriers are improved by the addition of PEG-modified lipids and, in particular, PEG-modified ceramide lipids. The addition of PEG-modified lipids prevents particle aggregation and provides a means for increasing circulation lifetime and increasing the delivery of the lipid-nucleic acid particles to the target cells. Moreover, it has been found that cationic lipids fuse more readily with the target cells and, thus, the addition of neutrally charged PEG-modified ceramide lipids does not mask or diminish the positive charge of the carrier liposomes.

Exemplary lipids useful for formulation of liposome include, but are not limited to:

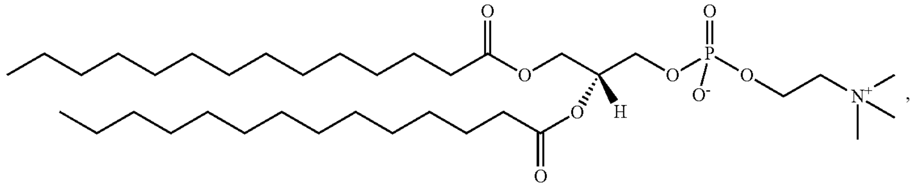

, 1,2-dimyristoyl-sn-glycero-3-phosphocholine (DMPC)

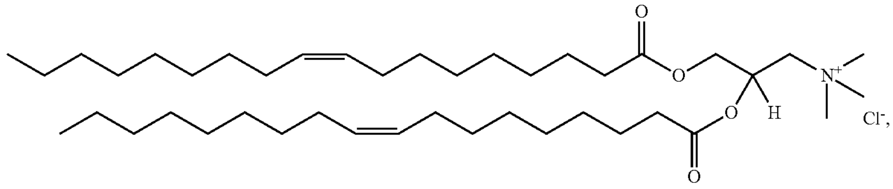

, 1,2-dioleoyl-3-trimethylammonium-propane (DOTAP)

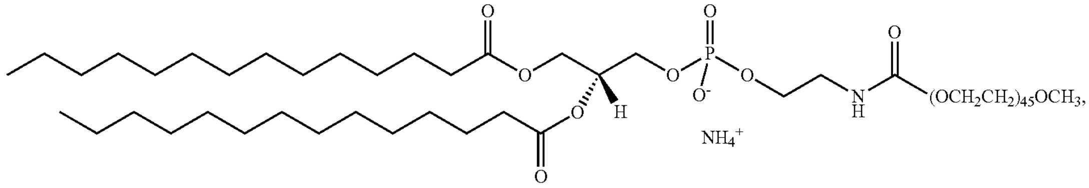

, 1,2-dimyristoyl-sn-glycero-3-phosphoethanolamine-N-[methoxy(polyethylene glycol)-2000] (PE-PEG2000 (methoxy))

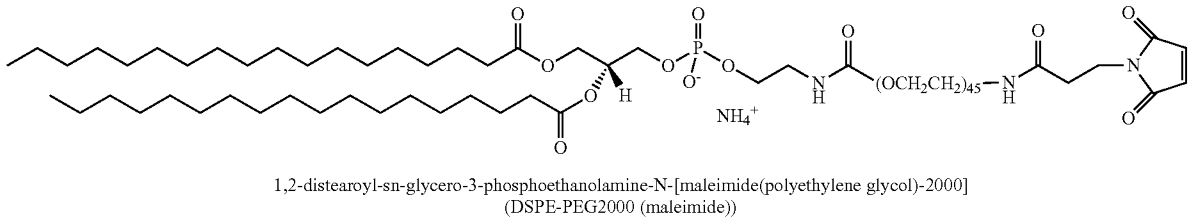

, 1,2-distearoyl-sn-glycero-3-phosphoethanolamine-N-[maleimide(polyethylene glycol)-2000] (DSPE-PEG2000 (maleimide))

-continued

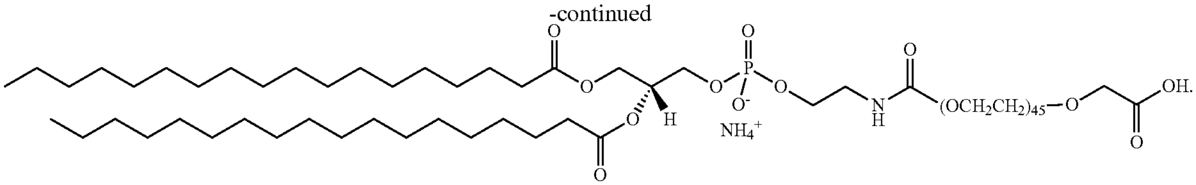

1,2-distearoyl-sn-glycero-3-phosphoethanolamine-N-[carboxy(polyethylene glycol)-2000]
(DSPE-PEG2000 (carboxy))

Figure 1C:
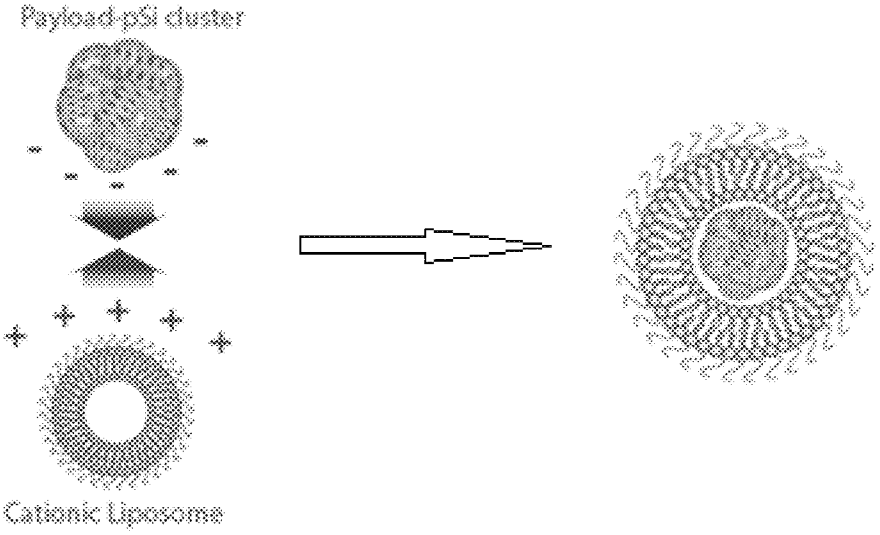
Figure 1D:
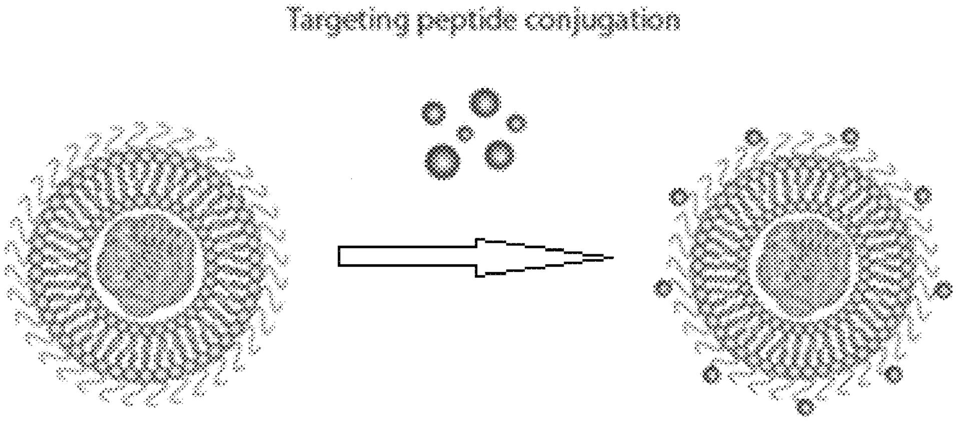
Figure 1E:
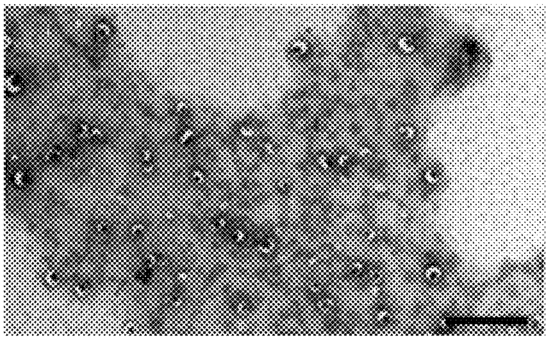

Generally, lipids dissolved in chloroform are mixed and solvent is evaporated to produce a dry film. In an embodiment where hydrophobic payload is embedded in the liposomal membrane, the hydrophobic payload solution is mixed with the lipid solution to be dried into the film together. The payload-entrapped porous silicon-based core is used to hydrate the fusogenic liposome film with gentle pipetting. The mixture will turn cloudy to indicate liposome formation. In some embodiments, the mixture can be heated at about 40° C. for 10 min before undergoing mechanical extrusion, e.g., 20 times through polycarbonate membrane with 200 nm pores. Excess payload is washed out by centrifugation three times with deionized water. FIG. 1B-D illustrates a schematic of the liposomal porous silicon nanoparticle synthesis. FIG. 1E depicts a schematic representation of a fusogenic liposomal porous silicon micro- and/or nanoparticle composition of the disclosure.

Typically the liposomal coating is comprised of pro-fusogenic lipids and moieties. For example, DMPC can acts as the structural backbone of the liposome, with a relatively low phase transition temperature ($T_m$=24° C.). The low transition temperature gives the $L_\alpha$ liquid crystal phase at room temperature and body temperature. The $L_\alpha$ phase is the more fluidic, dynamic, and permeable structure that allows for the wide size range (100-400 nm) of extruded liposomal coatings and an easier fusion potential. DOTAP is a cationic lipid useful for the electrostatic attraction toward the anionic plasma membrane. PEGylated lipids was also useful in fusion; though the exact mechanistic role of PEG is not yet known, it is hypothesized that PEG electrostatically binds water molecules to dehydrate the lipid head groups, which leads to structural asymmetry in the lipid alignment and drives double-leaflet to single-leaflet fusion as the energetically favorable route, similar to how SNARE proteins anchor and pull vesicles into merging with plasma membranes endogenously; in fact, neuronal SNAREs have been observed to promote PEG-mediated fusion.

It is further contemplated herein, that the liposomal layer encapsulating the silicon particle can be adapted for site-targeting, by tethering targeting moieties (peptides, aptamers, antibodies, antibody fragments, sugar or glycolipids) on or in the liposomal layer, which can guide the silicon particle and its cargo selectively to desired sites, thereby facilitating local drug delivery and therapeutic effects. For example, various reactive groups can be employed to tether targeting groups to the lipids making up the liposomes disclosed herein, such as sulfhydryl-reactive groups, maleimides, haloacetyls, pyridyldisulfides, thiosulfonates, and vinylsulfones; carboxyl-to-amine reactive groups, such as carbodiimides (e.g., EDC); amine-reactive groups, such as NHS esters, imidoesters, pentafluorophenyl esters, hydroxylmethyl phosphine; aldehyde-reactive groups, such as hydrazides, and alkoxyamines; photoreactive groups, such as diazinine, and aryl azide; and hydroxyl (nonaqueous)-reactive groups, such as isocyanates.

The targeting moieties bound to the surface of the liposome may vary from small haptens of from about 125-200 dalton molecular weight to much larger antigens with molecular weights of at least about 6 kD, but generally of less than $10^6$ kD. Proteinaceous ligand and receptors are of particular interest. Since agents/cargo incorporated in the silicon particles contained in the liposome may be indiscriminate with respect to cell type in its action, a targeted delivery system offers a significant improvement over randomly injecting non-specific liposomes.

A number of procedures can be used to covalently attach either polyclonal or monoclonal antibodies to a liposome bilayer. Antibody-targeted liposomes can include monoclonal or polyclonal antibodies or fragments thereof such as scFV, Fab, or $F(ab')_2$, so long as they bind efficiently to the antigenic epitope on the target cells.

As mentioned above, the disclosure also provides embodiments wherein the fusogenic liposome-coated nanoparticles comprise a targeting moiety/molecule. A targeting moiety/molecule can include, but is not limited to, a ligand or an antibody (including antibody fragments) that specifically binds to its corresponding target, for example, a receptor on a cell surface or an antigen. Thus, for example, where the targeting molecule is an antibody or fragment thereof, the fusogenic liposome-coated nanoparticles will specifically bind (target) cells and tissues bearing the epitope to which the antibody or antibody fragment is directed. Thus, a targeting molecule refers generally to all molecules capable of reacting with or otherwise recognizing or binding to a receptor or polypeptide on a target cell (e.g., it's cognate pair). Any known ligand or targeting molecule can be used. Examples of targeting peptides that can be manipulated and cloned or linked to produce a fusogenic liposome-coated nanoparticles are ample in the literature. In general, any peptide ligand can be used or fragments thereof based on the receptor-binding sequence of the ligand. In immunology, such a peptide domain is referred to as an epitope, and the term epitope may be used herein to refer to a ligand recognized by a receptor. For example, a ligand comprises the sequence of a protein or peptide that is recognized by a binding partner on the surface of a target cell, which for the sake of convenience is termed a receptor. However, it should be understood that for purposes of the disclosure, the term "receptor" encompasses signal-transducing receptors (e.g., receptors for hormones, steroids, cytokines, insulin, and other growth factors), recognition molecules (e.g., MHC molecules, B- or T-cell receptors), nutrient uptake receptors (such as transferrin receptor), lectins, ion channels, adhesion molecules, extracellular matrix binding proteins, and the like that are located and accessible at the surface of the target cell.

Various cell-types can be targeted. For example, antigen presenting cells (APCs), including leukocytes, may be targeted by making fusogenic liposome-coated nanoparticles comprising targeting molecules that recognize targets on the APCs. In operation, the fusogenic liposome-coated nanoparticles bind the targets fuse with the membrane, are internalized by the cells, and release the nanoparticle's contents into the cell. Examples of receptors that can be targeted or used as targeting moieties include, for example, the following receptors, or receptors for: E-selectin, CD3, CD 4, CD8, CD11, CD 14, CD 34, CD 123, CD 45Ra, CD64, E-cadherin, ICAM-1, interleukins, interferons, tumor necrosis factors, E-cadherin, Fc, MCH, CD 36 and other integrins, chemokines, Macrophage Mannose receptor and other lectin receptors, B7, CD's 40, 50, 80, 86 and other costimulatory molecules, Dec-205, scavenger receptors and toll receptors, see also Guermonprez et al. (Annu. Rev. Immunol., 2002).

The various embodiments provided herein are generally directed to systems and methods for producing a drug delivery device that can deliver cargo for treating or diagnosis of various diseases or disorders including viral and bacterial infections, cancers, tumors and other cell proliferative diseases and disorders, inflammatory diseases and disorders and tissue damage. In addition, the disclosure provides immunization techniques that boost drug delivery or promote drug action or improve immunogen processing associate with a silicon nanoparticle of the disclosure. Such methodology can include activating dendritic cells and other inflammatory cells and stimulating an immune response.

The composition comprising the liposome encapsulating the silicon nano- and/or micro-particle, can be formulated for enteral delivery, parenteral delivery, topical delivery, or by inhalation. The liposome-containing silicon particle of the disclosure can be formulated for in vitro and in vivo administration using techniques known in the art.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy to administer by a syringe. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is useful to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the liposomal silicon particle composition, e.g. a composition disclosed herein, in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In a particular embodiment, one or more liposomal formulations of the disclosure are prepared with carriers that will protect the compound against rapid elimination from the body, such as a controlled release formulation, including use of polyethylene glycol, implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc.

Data obtained from the cell culture assays and animal studies can be used in formulating a range of dosage for use in humans. A dose can be formulated in animal models to achieve a circulating plasma concentration range that includes the $IC_{50}$(e.g., the concentration of the test compound which achieves a half-maximal inhibition of symptoms) as determined in cell culture. Such information can be used to more accurately determine useful doses in humans. The methods and compositions of the disclosure are applicable to a wide range of species, e.g., humans, non-human primates, horses, cattle, pigs, sheep, goats, dogs, cats, rabbits, guinea pigs, hamsters, rats, and mice.

The liposomal silicon particle compositions and formulations disclosed herein, including pharmaceutical compositions comprising said formulations, can be used to treat any number of diseases or disorder that require delivery of a peptide, small molecule, nucleic acid (e.g., siRNA) into a cell.

The working examples below are provided to illustrate, not limit, the invention. Various parameters of the scientific methods employed in these examples are described in detail below and provide guidance for practicing the invention in general.

EXAMPLES

Fusogenic Silicon Nanoparticle Synthesis.

Fusogenic liposome films were made with a lipid solution in a mix of DMPC:DSPE-PEG:DOTAP at molar ratio of 76.2:3.8:20, along with the addition of 21 μL of 1.25 mg/ml of (2Z)-2-[(E)-3-(3,3-dimethyl-1-octadecylindol-1-ium-2-yl)prop-2-enylidene]-3,3-dimethyl-1-octadecylindole (DiI).

Porous silicon nanoparticles (pSiNPs) were prepared by electrochemical etching of single-crystal silicon wafers in an ethanolic aqueous HF solution followed by removal of the porous layer and ultrasonic fracture.

The liposomal mixture was dried into a film, and hydrated with the porous silicon or calcium silicate-deposited porous silicon nanoparticle solution. The hydrated suspension was heated to 40° C. under magnetic stirring for 20 min, and mechanically extruded twenty times through polycarbonate membrane with 200 nm pores.

FIG. 1B-H shows the particle synthesis schematic and characterization data. Scattering and microscopic data of the fusogenic liposome-coated pSi (F-pSi) confirm hydrodynamic diameter of approximately 190 nm. FIG. 1E-F show the particle characterization by transmission electron microscopy (TEM).

Drug Loading Into Porous Silicon Particles.

siRNA payloads were loaded within the pSi core cluster through calcium silicate sealing chemistry to approximately 20 wt % loading efficiency. Other oligonucleotide-loaded nanoplatforms, such as lipid-based nanoparticles and mesoporous silica-polymer hybrid systems, have an average loading efficient of 1-14 wt % (Table 1). In particular, comparably sized 200 nm particles can only load less than 5 wt % in these materials. Thus, the fusogenic porous silicon particles of the disclosure demonstrated a four-fold increase in oligonucleotide-loading efficiency, which can in turn enhance cellular gene knockdown efficiency.

TABLE 1 siRNA loading efficiency by wt. % comparison between Fusogenic pSiNPs and conventional platforms.

| Particle | Size | siRNA Loading (wt. %) |
| --- | --- | --- |
| Fusogenic liposome-coated pSiNP | 200 nm | 20-25% |
| Lipid-based Nanoparticles | 50-200 nm | 1-14% [41-51] |
| Mesoporous Silica-Polymer Hybrid NPs | 60-200 nm | 1-10% [52-55] |

In Vitro Uptake Behavior of Fusogenic Particles

Neuro2a cells were incubated with fusogenic liposomes and non-fusogenic liposomes for 1 h, and were visualized under confocal microscopy. Fusogenic particles transferred lipophilic DiI from the liposomal membrane to the plasma membrane to stain the cell outline, whereas non-fusogenic liposomes were found to localize in distinct groups in the cell cytoplasm, which is characteristic of endosomal or lysosomal compartmentalization.

Particles were loaded with hydrophilic (calcein) or lipophilic (DiI) dyes to evaluate differences in dye localization, and thus, particle uptake (FIG. 4). Calcein was chosen as the model-siRNA payload, as it is an anionic dye which typically cannot penetrate through the cell membrane, very similar to siRNA behavior. On the other hand, DiI was used as a way to confirm fusogenic uptake, as DiI is a lipophilic dye that is loaded into the liposomal bilayer. If the particle fuses upon uptake, the DiI would transfer and spread from the liposomal bilayer into the plasma membrane bilayer.

F-pSi loaded with DiI in the liposome membrane successfully transferred the DiI into the cell membrane and dispersed the calcein signal throughout the cell cytoplasm, indicating uptake via membrane fusion. In addition, minimal photoluminescence signal from the pSiNPs was detected-attributed to rapid degradation without liposomal protection post-fusion. On the other hand, non-fusogenic liposomal pSi (NF-pSi) loaded with DiI or calcein were localized dense clusters within the cell cytoplasm, indicating endocytosis. Moreover, calcein signals co-localized with pSi photoluminescence signals in concentrated spots. The psi signal indicates that the core remains intact with the calcein dye in endosomes/lysosomes due to liposomal protection. Since membrane fusion did not take place, we hypothesize that the liposome-coated pSi particle is endocytosed.

Using LysoTracker Red, the lysosomal intracellular compartments were stained as shown in FIG. 4 (*b*) and (*e*). The fusogenic and non-fusogenic particles were loaded with calcein and applied to cells. Results showed that while fusogenic particles showed dispersed calcein signals that did not co-localized with lysosomes, non-fusogenic particles showed calcein co-localization with lysosomal compartments. Further, DiI-loaded fusogenic and non-fusogenic particles conjugated with macrophage-targeting peptide (MTP) were prepared and treated to macrophages. The MTPs were also tagged with a 6-FAM dye to allow for fluorescence monitoring. Fusogenic particles were shown to fuse along specific parts of the cell membrane where MTP-FAM signals also co-localized, indicating that the MTP-FAM successfully anchors the particles to specific macrophage membrane receptors to allow for localized fusion. It is also notable that MTPs seemed to expedite the fusion process by quickly anchoring the particles to cell membrane surface, as only half the incubation time was needed to achieve comparable level of fusion. Non-fusogenic particles conjugated with MTP-FAM demonstrated the same localization as in the same particles without MTP. The MTP-FAM and DiI signals co-localized in clusters within the cytoplasm, indicative of endosomal and lysosomal compartmentalization.

Cell Impermeable Dye-Loaded Particles for Cytosolic Staining

Calcein is an anionic cell impermeable fluorescent dye. Due to its strong negative charge, it can be entrapped in porous silicon nanoparticles using the same calcium chloride interaction as nucleic acid payloads. Porous silicon particles were placed in an aqueous solution containing the Calcein and 1M or greater concentration of $CaCl_2$ solution. The solution was mixed and purified by centrifugation, resulting in Calcein-loaded calcium silicate coated porous silicon nanoparticles, or pSiNPs (Ca-pSi-Calcein). Unloaded Calcein was washed out by centrifugation three times in deionized water.

Figure 6:
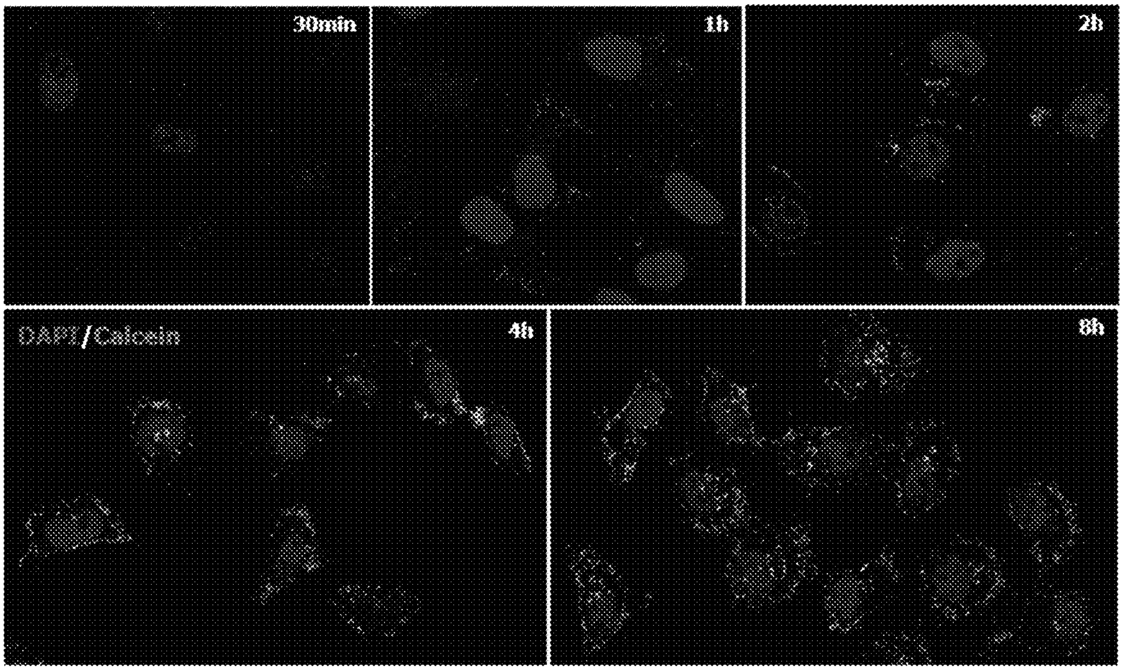
FIG. 6 shows confocal microscopy of HeLa cells up to 8 h of incubation with fusogenic liposome-coated particles.
Figure 7:
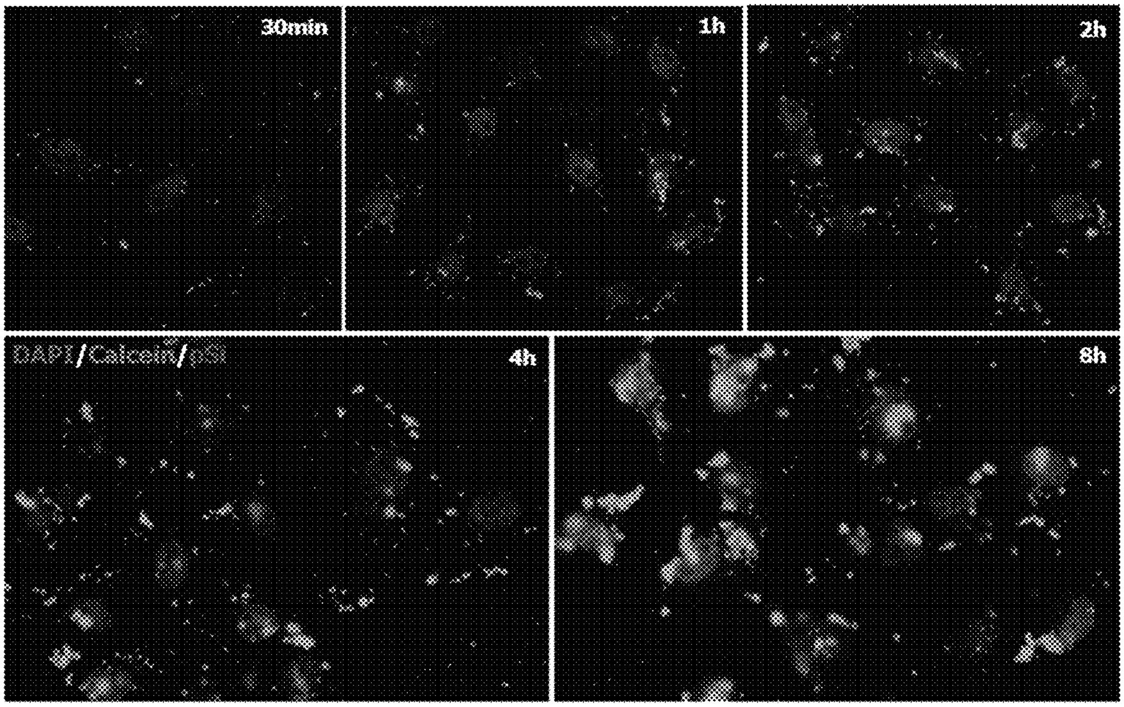
FIG. 7 shows confocal microscopy of HeLa cells up to 8 h of incubation with non-fusogenic liposome-coated particles.

HeLa cells were incubated with fusogenic liposome-coated particles and non-fusogenic liposome-coated particles, and were visualized under confocal microscopy over the following time intervals: 30 min, 1 h, 2 h, 4 h, and 8 h. Fusogenic liposome-coated particles were observed to release Calcein directly into the cell cytoplasm, and disperse them throughout the cell. The lack of red luminescence signal from porous silicon indicates its quick dissolution in the intracellular environment due to loss of shielding from liposome coating from the fusogenic uptake (FIG. 6). In contrast, non-fusogenic liposome-coated particles were co-localized with the calcein signals, in concentrated spots in the cytoplasm. The observation indicates that the non-fusogenic liposome-coated particles were endocytosed into the cells as a whole, and the maintenance of liposomal coating around the porous silicon-based core prevented core dissolution and loss of luminescence (FIG. 7).

In Vivo Gene Knockdown and Therapeutic Effect

Figure 8A:
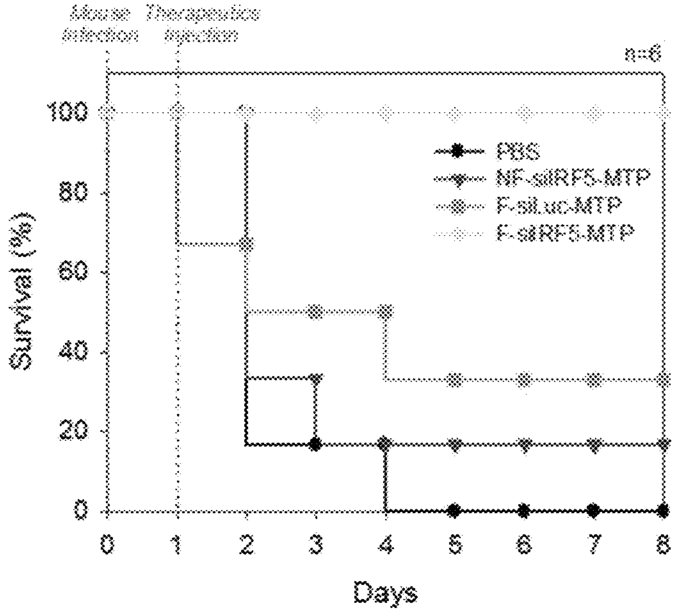
FIG. 8A-B shows (A) Mouse survival post-infection at day 0 and post-therapeutics injection (PBS, NF-siIRF5-MTP, F-siLuc-MTP, and F-siIRF5-MTP) at day 1. Each group has n=6 mice. (B) Average days of survival of mice post-infection at day 0 and post-therapeutic injection at day 1. Error bar indicates standard deviation. One-way ANOVA with Tukey's HSD post hoc test (a=0.05) revealed significant difference between F-siIRF5-MTP and the three control groups (PBS, NF-siIRF5-MTP, and F-siLuc-MTP).

Infected mice were tested with varying formulations to test for fusion and IRF5 knockdown effectiveness as anti-bacterial therapeutics. 6-week old female Balb/C mice were intratracheally infected with *Staph. aureus* bacteria 24 h prior to intravenous tail-vein injection of saline (PBS), targeted non-fusogenic particles loaded with therapeutic siRNA (NF-siIRF5-MTP), targeted fusogenic particles loaded with control non-therapeutic siRNA (F-siLuc-MTP), or targeted fusogenic particles loaded with therapeutic siRNA (F-siIRF5-MTP). The mice were observed for 7 days following treatment for survival, and tallied to obtain the results shown in FIG. 8A.

Figure 8B:
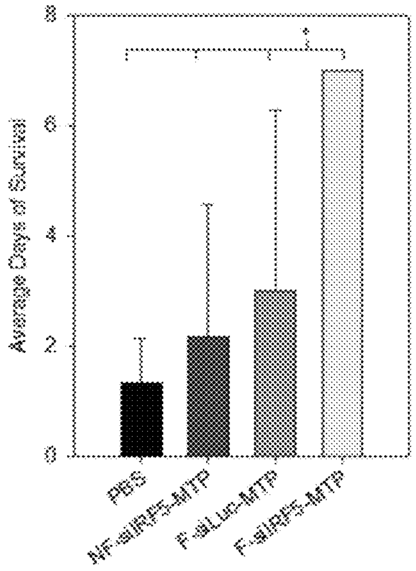

FIG. 8B shows the average days of survival from each treatment group, and the statistical significance. From single way ANOVA and post hoc comparisons using Tukey's HSD test, the data show that mice injected with F-siIRF5-MTP particles had significantly higher average number of survival days than all other formulations, PBS, NF-siIRF5-MTP, and F-siLuc-MTP (p level$<$0.05, [F (3, 20)=8.78, p=0.001].

In all treatment groups, mice surviving past 4 days showed normal healthy behavior and no visible outward signs of distress or illness.

Fusogenic Silicon Particle Stability

Figure 9:
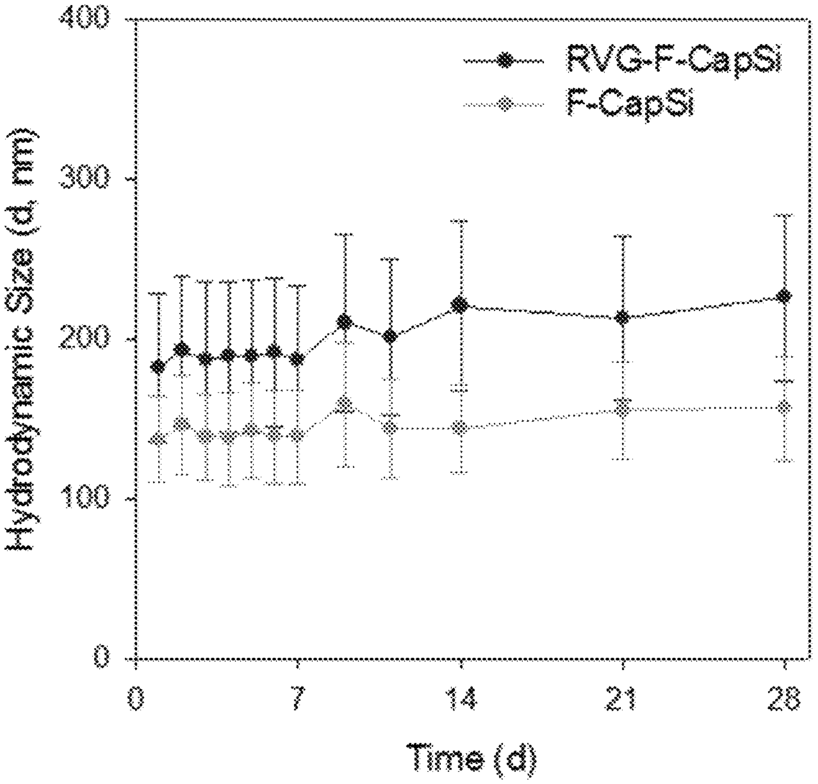
FIG. 9 shows month-long observation of average hydrodynamic diameter of fusogenic liposome-coated calcium silicate porous silicon nanoparticles (F-CapSi) and RVG-conjugated fusogenic liposome-coated calcium silicate porous silicon nanoparticles (RVG-F-CapSi) by DLS.

The particle stabilities in phosphate-buffered saline (PBS) was observed for 28 days by measuring hydrodynamic diameter changes by DLS (FIG. 9). Fusogenic liposome-coated particles (F-CapSi) were extruded to an initial average hydrodynamic diameter of approximately 140 nm. RVG-conjugation to the maleimide-terminated PEG (RVG-F-CapSi) extended the size to approximately 180 nm. The size remained highly stable for the first 7 days, before increasing gradually over the next 3 weeks.

Antibody-Conjugated Particles

Antibodies can be conjugated to the surface of the liposome by a similar PEG interaction used with targeting peptide conjugations. A fusogenic liposome film was made of mix of DMPC:DSPE-PEG (carboxy):DOTAP at molar ratio of 76.2:3.8:20. The mixture was dried into a film, and hydrated with porous silicon or metal (Ca) silicate-deposited porous silicon nanoparticle solution. The hydrated suspension was heated to 40° C. under magnetic stirring for 20 min, and mechanically extruded twenty times through polycarbonate membrane with 200 nm pores. The amine group on the lysine residue of the Fc region of the antibody was conjugated to the carboxyl-terminated PEG to form an amide bond via 1-ethyl-3-(3-dimethylaminopropyl)carbodiimide/sulfo-N-hydroxysuccinimide (EDC/sulfo-NHS) chemistry.

In order to verify cellular uptake by membrane fusion, lipophilic (2Z)-2-[(E)-3-(3,3-dimethyl-1-octadecylindol-1-ium-2-yl)prop-2-enylidene]-3,3-dimethyl-1-octadecylindole (DiI) fluorescent dye, was loaded into the liposomal membrane. Particles were treated to Neuro2a cells, and incubated for 1 h for cellular uptake. Fusogenic particles were able to successfully transfer the lipophilic DiI from the liposomal membrane to the plasma membrane, whereas particles coated with non-fusogenic liposomes were found to localize in distinct groups in the cell cytoplasm, which is characteristic of endosomal/lysosomal uptake (FIG. 12, left panel).

Figure 10:
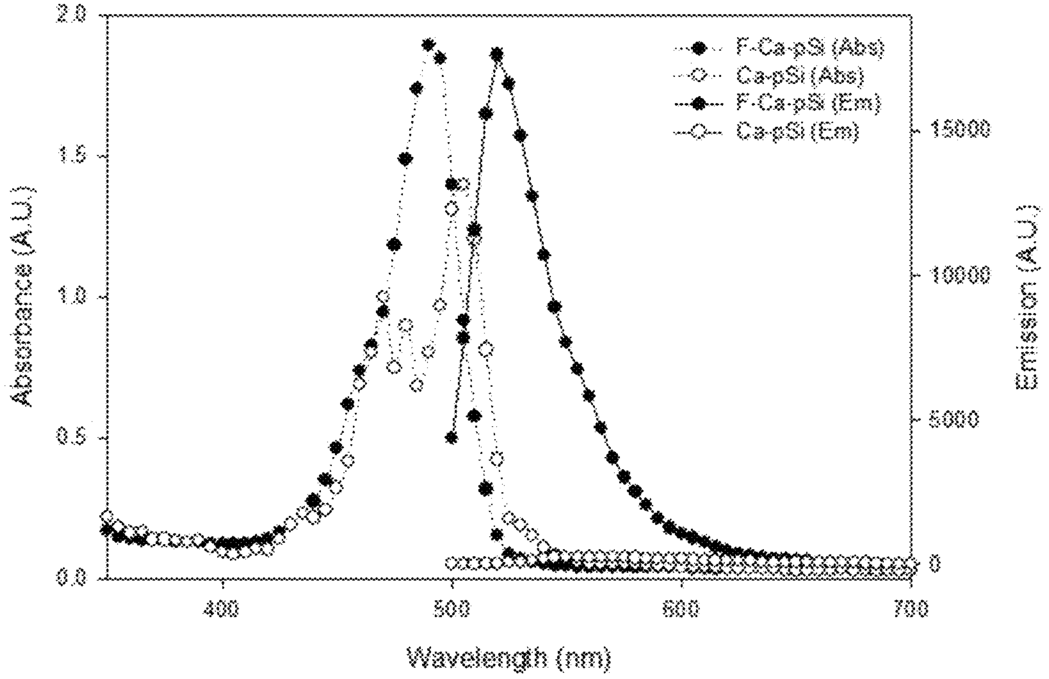
FIG. 10 shows absorbance (dotted) and emission (solid) spectra of Calcein loaded in fusogenic liposome-coated calcium silicate porous silicon nanoparticles (F-Ca-pSi) and non-coated calcium silicate porous silicon nanoparticles (Ca-pSi).

Next, the difference between fusogenic and non-fusogenic liposomal coating in intracellular localization of hydrophilic payloads were investigated. Calcein, a highly anionic cell-impermeable dye was loaded within the porous silicon core using calcium chloride entrapment, and encapsulated in fusogenic and non-fusogenic liposomes. FIG. 10 shows the absorbance and fluorescence spectra of Calcein loaded in liposome-coated particles. Liposomal encapsulation of Calcein-loaded particles allowed de-quenching of the fluorescence emission.

Figure 11:
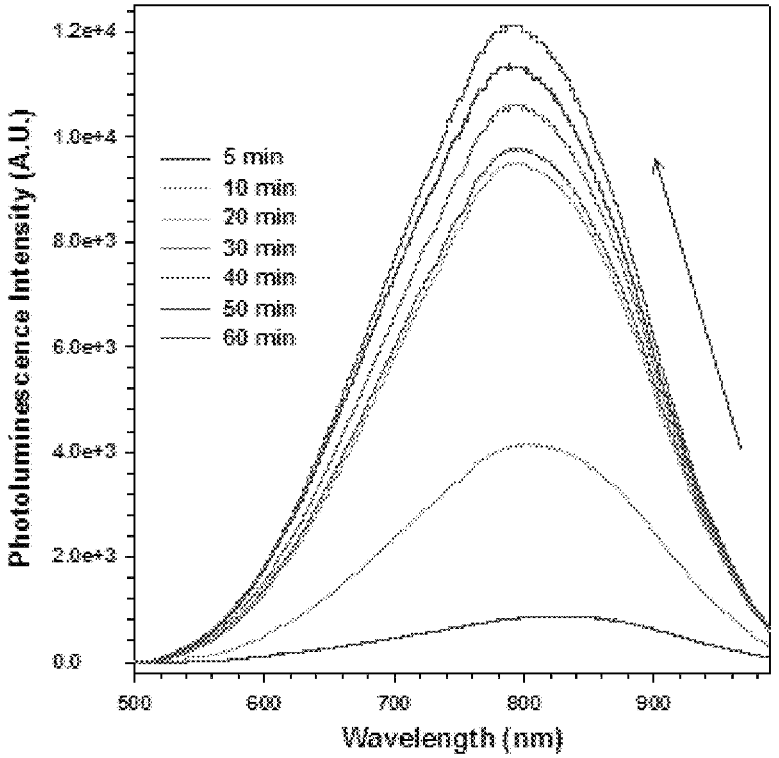
FIG. 11 shows photoluminescence spectra obtained over reaction time of pSiNPs and $CaCl_2$ (or $MgCl_2$) solution.

The photoluminescence of calcium silicate-coated particles was also studied; the calcium silicate/silicon oxide shell or magnesium silicate/silicon oxide shell displays a strong ability to passivate the surface of the silicon nanostructures, yielding increased intrinsic photoluminescence from the material. FIG. 11 shows photoluminescence spectra obtained at different times during the course of the reaction between pSiNPs and CaCl2) (or MgCl2) solution. During the reaction, the intensity of photoluminescence gradually increased, attributed to the passivation of nan-radiative carrier traps on the pSiNP surface. Additionally, the peak wavelength of photoluminescence showed a pronounced blue shift as the reaction progressed. Both these phenomena (increase in photoluminescence intensity and blue shift of the photoluminescence spectrum) are indicative of the growth of a passivating surface layer on the silicon nanocrystallites. The observed blue shift is typical of a quantum confined nanoparticle, whose emission wavelength is strongly dependent on size and expected to blue shift as the quantum confined silicon domains become smaller. Because it is intimately tied to the host silicon matrix, the intrinsic photoluminescence of the nanoconstruct can be used to monitor degradation of the matrix and, by inference, the release of payload in an in vitro or in vivo experiment.

The particles were treated to HeLa cells and visualized under confocal microscopy over time. The right panel on FIG. 12 shows the cellular uptake of the particles after 8 h of incubation. Fusogenic liposome-coated particles were observed to release the Calcein payload into the cell cytoplasm, and disperse them throughout the cell. The lack of luminescence signal from calcium silicate-coated porous silicon indicates its quick dissolution in the intracellular environment due to lack of shielding from fused liposome. In contrast, non-fusogenic liposome-coated particles were co-localized with the calcein signals, in concentrated spots in the cytoplasm. The observation indicates that the non-fusogenic liposome-coated particles were endocytosed into the cells as a whole, and the maintenance of liposomal coating around the porous silicon-based core prevented core dissolution.

Targeting Peptide-Conjugated Particles

Rabies virus glycoprotein (RVG, (CCGG)YTIWMPEN PRPGTPCDIFTNSRGKRASNG (SEQ ID NO:1)) is a Neuro2a mouse neuroblast-targeting peptide, which is conjugated to the maleimide-terminated PEG of the liposomal coat via maleimide-thiol/cysteine covalent binding interaction. To observe interactions with cells under confocal microscopy, the RVG peptide was tagged with 5-FAM dye, and the liposomal membrane with lipophilic DiI. Targeting-peptide conjugation did not seem to affect fusogenicity of the liposome coating, and were only observed to accelerate fusion and uptake rate compared to the fusogenic liposome-coated particles without targeting peptide.

siRNA-Loaded Particles for Gene Knockdown

Small interfering RNA (siRNA) cargo was loaded into the porous silicon core by mixing the porous silicon particles with siRNA dissolved in deionized water and 3M $CaCl_2$ and washing by centrifugation.

Figure 14:
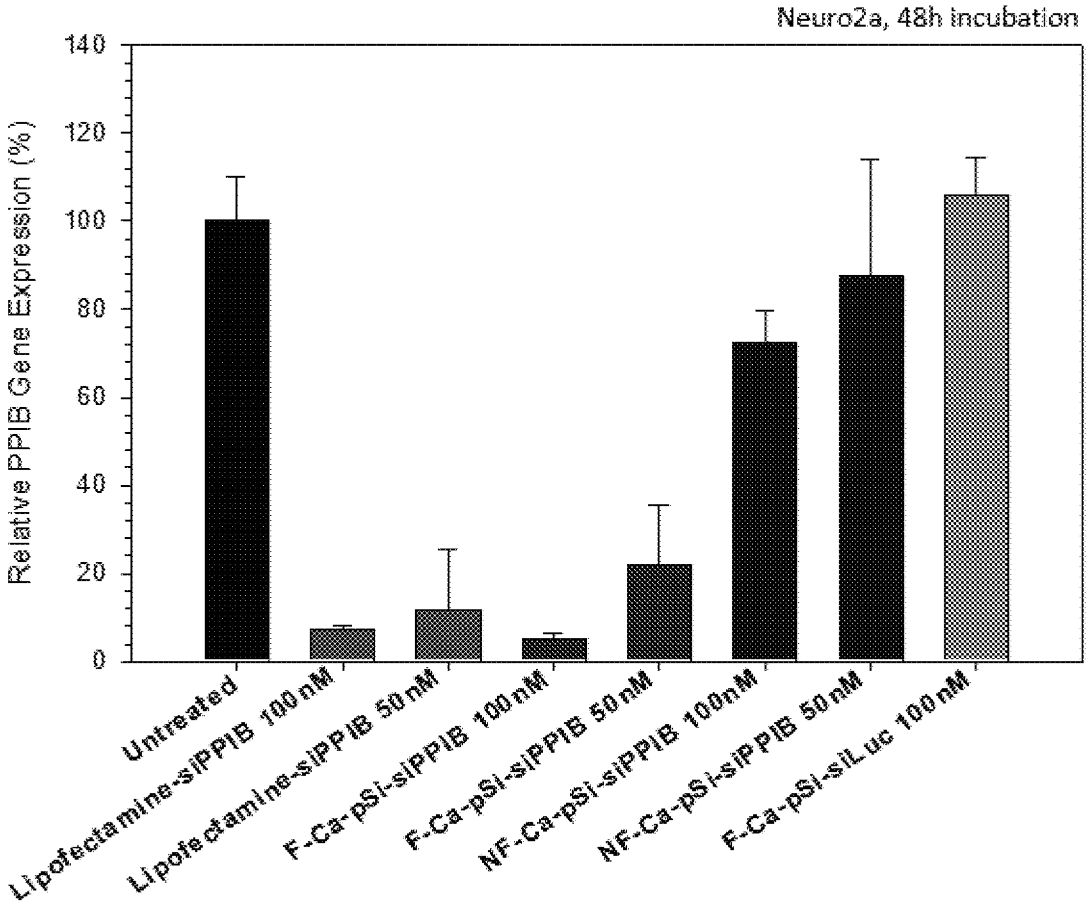
FIG. 14 shows siRNA knockdown results from 48 h incubation of particles in Neuro2a mouse neuroblastoma cells. F-Ca-pSi-siPPIB: Fusogenic liposome-coated calcium silicate porous silicon nanoparticles loaded with siRNA against PPIB; NF-Ca-pSi-siPPIB: Non-fusogenic liposome-coated calcium silicate porous silicon nanoparticles loaded with siRNA against PPIB; F-Ca-pSi-siLuc: Fusogenic liposome-coated calcium silicate porous silicon nanoparticles loaded with siRNA against luciferase.

For siRNA knockdown test in Neuro2a cells, peptidyl-prolyl isomerase B (PPIB/siPPIB) was chosen as the target gene (FIG. 14). The siPPIB-loaded F-pSi demonstrated knockdown efficiency of approximately 95% at 100 nM. By contrast, the common transfection agent lipofectamine achieved only 90% knockdown efficiency under similar conditions. The non-fusogenic control nanoparticles NF-pSi demonstrated only 30% knockdown 100 nM, with high variability.

In Vivo Macrophage-Targeting and Infection Homing

Balb/C mice were intratracheally infected with *Staph. aureus* to induce lung infection. A macrophage/monocyte-targeting peptide was attached to the F/NF-pSi loaded with calcein and DiI, and the formulations were administered into *Staph. aureus* infected mice via intravenous injection, to observe for targeting efficacy to macrophages and the macrophage homing to the infected lungs (FIG. 15). Harvested lungs of mice injected with calcein-loaded particles were homogenized for FACS quantification of calcein accumulation in infected lungs, as shown in FIG. 15 (*a-c*). Lungs of mice injected with DiI-loaded particles were fixed for fluorescence histological evaluation, as shown in FIG. 15 (*d-k*). Despite targeting peptide attachment, NF-pSi showed no visible homing to lungs in both Calcein-loaded FACs data and the DiI-loaded fluorescent histological evaluation. F-pSi without targeting peptide showed minimal accumulation in both assessments, whereas F-pSi with targeting peptide demonstrated clear targeting to macrophages and subsequent homing to infected lungs in both FACS and fluorescent histology. Thus, the macrophage-targeting peptide is necessary in in vivo homing of nanoparticles to macrophages.

With the MTP targeting peptide conjugation as described herein, the nanoparticles loaded with either Calcein or DiI were able to successfully home to the infected lung, whereas particles without the MTP peptide and the non-fusogenic particles could not. Healthy lungs also showed no visible homing, as there are fewer macrophages that are recruited. With the validation that the MTP peptide homing in infected lungs, formulations loaded with therapeutic siIRF5 was tested for therapeutic efficacy.

The disclosure demonstrates that fusogenic liposome-coated pSi system are able to bypass endocytosis to achieve greater gene knockdown efficacy compared to non-fusogenic formulations. Furthermore, in vivo targeting to macrophages/monocytes was successfully demonstrated, and the payload-delivered macrophage/monocytes homed effectively to infected lungs. With M1 phenotype-suppressive siRNA delivery to the macrophages, that data show that the fusogenic system can achieve improved and effective immunogenic clearance of infection potentially due to higher phagocytic activity, inflammation mitigation, and tissue-healing.

A number of embodiments of the invention have been described. Nevertheless, it will be understood that various modifications may be made without departing from the spirit and scope of the invention. Accordingly, other embodiments are within the scope of the following claims.

What is claimed is:

1. A method of preparing a fusogenic liposome-coated porous silicon nanoparticle comprising the steps of:

(a) etching a crystalline silicon wafer or powder to generate a porous silicon nanostructured material, (b) optionally fracturing the porous silicon nanostructured material, (c) treating the porous silicon nanostructured material with a molecular cargo, (d) treating the porous silicon nanostructured material with a metal salt to form a metal silicate on a surface of the porous silicon nanostructured material, wherein the metal salt has a concentration of at least 1 molar, and (e) treating the porous silicon nanostructured material with a fusogenic lipid.

2. The method of claim 1, further comprising the step of oxidizing the porous silicon nanostructured material.

3. The method of claim 1, wherein the metal salt is a calcium or magnesium salt.

4. The method of claim 1, wherein the fusogenic lipid comprises a phosphatidylcholine, a phosphatidic acid, a phosphatidylethanolamine, a phosphatidylglycerol, a phosphatidylserine, a lysophosphatidylcholine, or a derivative thereof.

5. The method of claim 1, wherein the fusogenic lipid comprises a cationic lipid.

6. The method of claim 1, wherein the fusogenic lipid comprises a PEGylated lipid.

7. The method of claim 1, wherein the fusogenic lipid comprises a mixture of DMPC, DOTAP, and DSPE-PEG (methoxy).

8. The method of claim 1, wherein the fusogenic lipid comprises a mixture of DMPC, DOTAP, and DSPE-PEG (carboxy).

9. The method of claim 1, wherein the fusogenic lipid comprises a mixture of DMPC, DOTAP, and DSPE-PEG (maleimide).

10. The method of claim 1, wherein the fusogenic liposome-coated porous silicon nanoparticle has a hydrodynamic diameter ranging from about 10-100 nm.

11. The method of claim 1, wherein the fusogenic liposome-coated porous silicon nanoparticle has a hydrodynamic diameter ranging from about 100-400 nm.

12. The method of claim 1, wherein the molecular cargo is a nucleic acid.

13. The method of claim 12, wherein the nucleic acid is an RNA.

14. The method of claim 1, wherein the molecular cargo is a small molecule drug.

15. The method of claim 1, wherein the molecular cargo is a peptide or a protein.

16. The method of claim 1, wherein the etching is an electrochemical etching or a stain etching.

17. The method of claim 1, further comprising the step of treating the porous silicon nanoparticle core material with a targeting molecule.

18. The method of claim 17, wherein the targeting molecule is an antibody or a targeting peptide.

* * * * *

```
                    SEQUENCE LISTING


Sequence total quantity: 1
SEQ ID NO: 1            moltype = AA  length = 33
FEATURE                 Location/Qualifiers
source                  1..33
                        mol_type = protein
                        organism = Rabies virus
SEQUENCE: 1
CCGGYTIWMP ENPRPGTPCD IFTNSRGKRA SNG                            33
```